(12) United States Patent
Harrison et al.

(10) Patent No.: US 6,221,657 B1
(45) Date of Patent: Apr. 24, 2001

(54) MODIFIED HUMAN C3 DNA SEQUENCES AND VECTORS

(75) Inventors: Richard Alexander Harrison; Timothy Charles Farries, both of Cambridge (GB)

(73) Assignee: Imutran Limited (GB)

( * ) Notice: Subject to any disclaimer, the term of this patent is extended or adjusted under 35 U.S.C. 154(b) by 0 days.

(21) Appl. No.: 09/132,271

(22) Filed: Aug. 11, 1998

Related U.S. Application Data

(62) Division of application No. 08/793,126, filed on Feb. 7, 1997, now Pat. No. 5,849,297, which is a continuation of application No. PCT/GB95/02121, filed on Sep. 8, 1995.

(51) Int. Cl.[7] ............................. C12N 15/57; C12N 15/63; C12N 9/64
(52) U.S. Cl. .................... 435/320.1; 536/23.2; 536/23.5; 435/69.6; 435/226; 530/380
(58) Field of Search .................................. 536/23.5, 23.2; 435/320.1, 69.6, 226; 530/380

(56) References Cited

U.S. PATENT DOCUMENTS

| 4,661,347 | 4/1987 | Muller-Eberhard et al. ........ 424/85 |
| 5,928,892 | * 7/1999 | Hourcade et al. ................. 435/69.1 |

OTHER PUBLICATIONS

R.R. Kew et al., J. Clin. Invest., 75:1000–1007 (1985).
D.E. Isenman et al., Biochemistry, 20(15):4458–4467 (1981).
Z. Fishelson et al., J. Immunol., 132(3):1430–1434 (1984).

* cited by examiner

Primary Examiner—Rebecca E. Prouty

(57) ABSTRACT

This invention is directed to DNA sequences encoding narrative complement pathway proteins modified such that the protein is capable of forming a stable C3 convertase. The modified C3 proteins are useful in therapy.

**10 Claims, 15

Figure 3:
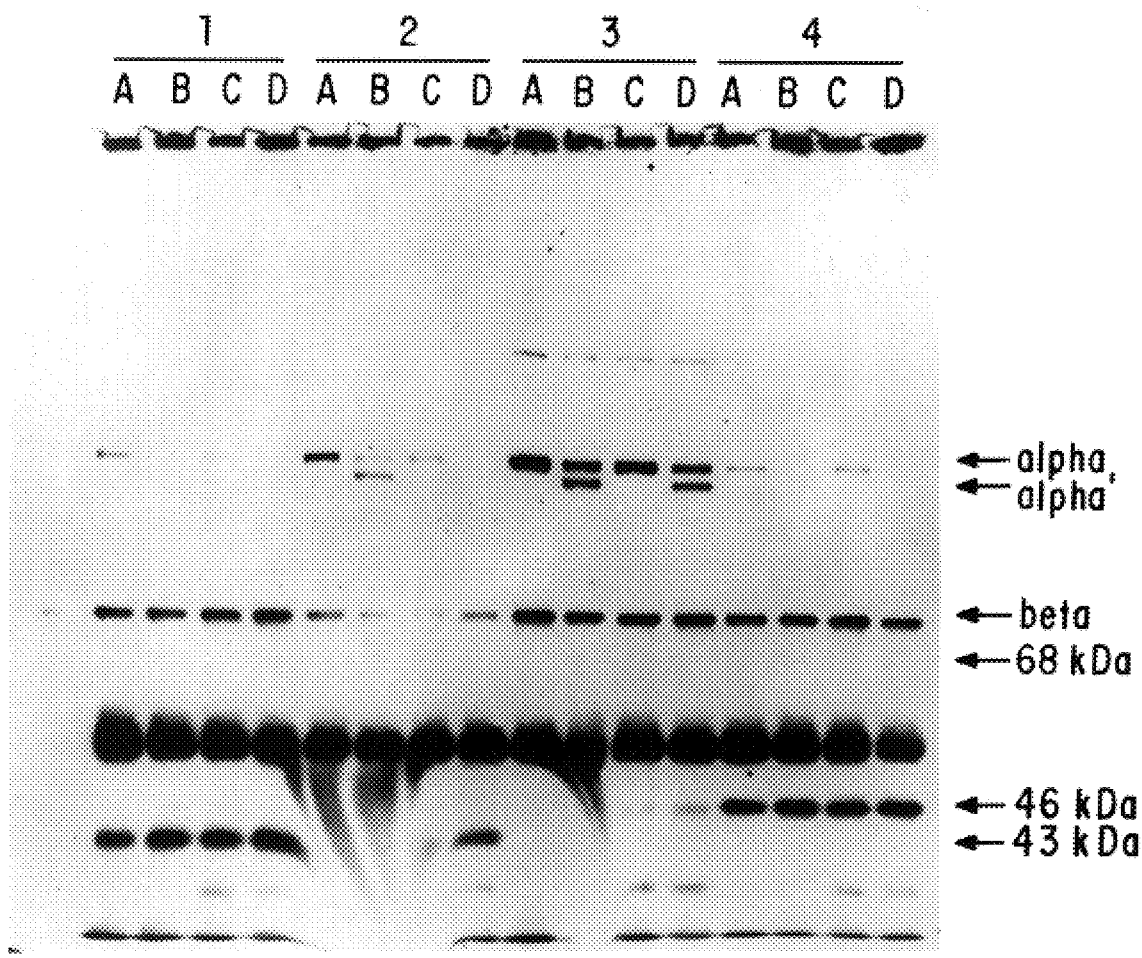

```
            10         20          30         40          50         60
   MGPTSGPSLL LLLLTHLPLA  LGSPMYSIIT PNILRLESEE  TMVLEAHDAQ GDVPVTVTVH 70         80          90        100         110        120
   DFPGKKLVLS SEKTVLTPAT  NHMGNVTFTI PANREFKSEK  GRNKFVTVQA TFGTQVVEKV 130        140         150        160         170        180
   VLVSLQSGYL FIQTDKTIYT  PGSTVLYRIF TVNHKLLPVG  RTVMVNIENP EGIPVKQDSL 190        200         210        220         230        240
   SSQNQLGVLP LSWDIPELVN  MGQWKIRAYY ENSPQQVFST  EFEVKEYVLP SFEVIVEPTE 250        260         270        280         290        300
   KFYYIYNEKG LEVTITARFL  YGKKVEGTAF VIFGIQDGEQ  RISLPESLKR IPIEDGSGEV 310        320         330        340         350        360
   VLSRKVLLDG VQNPRAEDLV  GKSLYVSATV ILHSGSDMVQ  AERSGIPIVT SPYQIHFTKT 370        380         390        400         410        420
   PKYFKPGMPF DLMVFVTNPD  GSPAYRVPVA VQGEDTVQSL  TQGDGVAKLS INTHPSQKPL 430        440         450        460         470        480
   SITVRTKKQE LSEAEQATRT  MQALPYSTVG NSNNYLHLSV  LRTELRPGET LNVNFLLRMD 490        500         510        520         530        540
   RAHEAKIRYY TYLIMNKGRL  LKAGRQVREP GQDLVVLPLS  ITTDFIPSFR LVAYYTLIGA 550        560         570        580         590        600
   SGQREVVADS VWVDVKDSCV  GSLVVKSGQS EDRQPVPGQQ  MTLKIEGDHG ARVVLVAVDK 610        620         630        640         650        660
   GVFVLNKKNK LTQSKIWDVV  EKADIGCTPG SGKDYAGVFS  DAGLTFTSSS GQQTAQRAEL 670        680         690        700         710        720
   QCPQPAARRR RSVQLTEKRM  DKVGKYPKEL RKCCEDGMRE  NPMRFSCQRR TRFISLGEAC 730        740         750        760         770        780
   KKVFLDCCNY ITELRRQHAR  ASHLGLARSN LDEDIIAEEN  IVSRSEFPES WLWNVEDLKE 790        800         810        820         830        840
   PPKNGISTKL MNIFLKDSIT  TWEILAVSMS DKKGICVADP  FEVTVMQDFF IDLRLPYSVV 850        860         870        880         890        900
   RNEQVEIRAV LYNYRQNQEL  KVRVELLHNP AFCSLATTKR  RHQQTITIPP KSSLSVPYVI 910        920         930        940         950        960
   VPLKTGLQEV EVKAAVYHHF  ISDGVRKSLK VVPEGIRMNK  TVAVRTLDPE RLGREGVQKE
```

FIG.1A

```
          970        980        990       1000       1010       1020
   DIPPADLSDQ VPDTESETRI LLQGTPVAQM TEDAVDAERL KHLIVTPSGC GEQNMIGMTP 1030       1040       1050       1060       1070       1080
   TVIAVHYLDE TEQWEKFGLE KRQGALELIK KGYTQQLAFR QPSSAFAAFV KRAPSTWLTA 1090       1100       1110       1120       1130       1140
   YVVKVFSLAV NLIAIDSQVL CGAVKWLILE KQKPDGVFQE DAPVIHQEMI GGLRNNNEKD 1150       1160       1170       1180       1190       1200
   MALTAFVLIS LQEAKDICEE QVNSLPGSIT KAGDFLEANY MNLQRSYTVA IAGYALAQMG 1210       1220       1230       1240       1250       1260
   RLKGPLLNKF LTTAKDKNRW EDPGKQLYNV EATSYALLAL LQLKDFDFVP PVVRWLNEQR 1270       1280       1290       1300       1310       1320
   YYGGGYGSTQ ATFMVFQALA QYQKDAPDHQ ELNLDVSLQL PSRSSKITHR IHWESASLLR 1330       1340       1350       1360       1370       1380
   SEETKENEGF TVTAEGKGQG TLSVVTMYHA KAKDQLTCNK FDLKVTIKPA PETEKRPQDA 1390       1400       1410       1420       1430       1440
   KNTMILEICT RYRGDQDATM SILDISMMTG FAPDTDDLKQ LANGVDRYIS KYELDKAFSD 1450       1460       1470       1480       1490       1500
   RNTLIIYLDK VSHSEDDCLA FKVHQYFNVE LIQPGAVKVY AYYNLEESCT RFYHPEKEDG 1510       1520       1530       1540       1550       1560
   KLNKLCRDEL CRCAEENCFI QKSDDKVTLE ERLDKACEPG VDYVYKTRLV KVQLSNDFDE 1570       1580       1590       1600       1610       1620
   YIMAIEQTIK SGSDEVQVGQ QRTFISPIKC REALKLEEKK HYLMWGLSSD FWGEKPNLSY 1630       1640       1650       1660
   IIGKDTWVEH WPEEDECQDE ENQKQCQDLG AFTESMVVFG
```

FIG.1B

```
          cctctccct ctgtccctct gtccctctga cactgcactg tcccagcacc
          12        20         30         40         50         60 atgggaccca cctcaggtcc cagcctgctg ctcctgctac taacccacct cccccotggct
70         80         90         100        110        120 ctggggagtc ccatgtactc tatcatcacc cccaacatct tgaggatgga gagcgaggag
130        140        150        160        170        180 accatggtgc tggaggccca cgacgcgcaa ggggatgttc cagtcactgt tactgtccac
190        200        210        220        230        240 gacatcccag gcaaaaaact agtgatgtcc agtgagaaga ctgtgctgac ccctgacacc
250        260        270        280        290        300 aaccacatgg gaaacgtcac cttcacgatc ccagccaaca gggagttcaa gtcagaaaag
310        320        330        340        350        360 gggcgcaaca agtacgtgac cgtgcaggcc accttcggga cccaagtggt ggagsaggtg
370        380        390        400        410        420 gtgctggtca gcctgcagag cgggtacctc tccatccaga cagacaagac catctacacc
430        440        450        460        470        480 cctggctcca cagttctcta taggatcttc accgccaacc acaagctgat acccgtgggc
490        500        510        520        530        540 cggacggtca tggtcaacat tgagaacccg gaaggcatcc cggtcaagca ggactccttg
550        560        570        580        590        600 tcttatcaga accagcttgg cgtcttgccc ttgtcttggg acattccgga actcgacaac
610        620        630        640        650        660 atgggccagt ggaagatccg agcctactat gcaaactcac cacagcaggt cttctccact
670        680        690        700        710        720 gagtttgagg tgaaggagta cgtgctgccc agtttcgagg tcatagtgga gactacagag
730        740        750        760        770        780 aaatcatact acatctataa cgagaagggc ctggaggtca ccatcacagc caggatcctc
790        800        810        820        830        840 taagggaaga aagtggaggg aactgccttt gtcatattcg ggatccagga tggcgaacag
850        860        870        880        890        900 aggattcccc tgcctgaatc cctcaagcgc atcccgattg aggatggctc gggggaggtt
910        920        930        940        950        960
```

FIG.2A

| | | | | | |
|---|---|---|---|---|---|
| gtgctgagcc 970 | ggaaggtact 980 | gctggacggg 990 | gtgcagaacc 1000 | ccagagcaga 1010 | agacctggtg 1020 |
| gggaagtctt 1030 | tgtacgtgtc 1040 | tgccaccgtc 1050 | atcttgaact 1060 | caggcagtga 1070 | catggtgcag 1080 |
| gcagagcgca 1090 | gcgggatccc 1100 | catcgtgacc 1110 | tctccctacc 1120 | agatccactt 1130 | caccaagaca 1140 |
| cccaagtact 1150 | tcaaaccagg 1160 | aatgcccttt 1170 | gacctcatgg 1180 | tgttcgtgac 1190 | gaaccctgat 1200 |
| ggatctccag 1210 | cctacagagt 1220 | ccaagtggca 1230 | gtccagggag 1240 | aggacactgt 1250 | gcagtctcta 1260 |
| acccagggag 1270 | atggcgtggc 1280 | caaactcagc 1290 | atcaacacac 1300 | accccagcca 1310 | gaagcccttg 1320 |
| agcatcacgg 1330 | tgcgcacgaa 1340 | gaagcaggag 1350 | ctctcggagg 1360 | cagagcaggc 1370 | taccaggacc 1380 |
| atgcaggctc 1390 | tgccctacag 1400 | caccgtgggc 1410 | aactccaaca 1420 | attacctgca 1430 | tctctcagtg 1440 |
| ctacgtacag 1450 | agatcagacc 1460 | cggggagacc 1470 | ctcaacgtca 1480 | acttcctcct 1490 | gcgaatggac 1500 |
| cgcgcccacg 1510 | aggccaagat 1520 | ccgctactac 1530 | acctacctga 1540 | tcatgaacaa 1550 | gggcaggctg 1560 |
| ttgaaggcgg 1570 | gacgccaggt 1580 | gcgagagccc 1590 | ggccaggacc 1600 | tggtggtgct 1610 | gccctgtcc 1620 |
| atcaccaccg 1630 | acttcatccc 1640 | tcccttccgc 1650 | ctggtggcgt 1660 | actacacgct 1670 | gatcggtgcc 1680 |
| agcggccaga 1690 | gggaggtggt 1700 | ggccgactcc 1710 | gtgtgggtgg 1720 | acgtcaagga 1730 | ctcctgcgtg 1740 |
| ggctcgctgg 1750 | tggtaaaaag 1760 | cggccagtca 1770 | gaagaccggc 1780 | agcctgtacc 1790 | tgggcagcag 1800 |
| atgaccctga 1810 | agatagaggg 1820 | tgaccacggg 1830 | gcccggggtgg 1840 | tactggtggc 1850 | cgtggacaag 1860 |
| ggcgtgttcg 1870 | tgctgaataa 1880 | gaagaacaaa 1890 | ctgacgcaga 1900 | gtaagatctg 1910 | ggacgtggtg 1920 |

FIG.2B

```
gagaaggcag  acatcggctg  cacccgggc   agtgggaagg  attacgccgg  tgtcttctcc
     1930        1940        1950        1960        1970        1980 gacgcagggc  tgaccttcac  gagcagcagt  ggccagcaga  ccgcccagag  ggcagaactt
     1990        2000        2010        2020        2030        2040 cagtgcccgc  agccagccgc  ccgccgacgc  cgttccgtgc  agctcacgga  gaagcgaatg
     2050        2060        2070        2080        2090        2100 gacaaagtcg  gcaagtaccc  caaggagctg  cgcaagtgct  gcgaggaccg  catgcgggag
     2110        2120        2130        2140        2150        2160 aaccccatga  ggttctcgtg  ccagcgccgg  acccgttcca  tctccctggg  cgaggcgtgc
     2170        2180        2190        2200        2210        2220 aagaaggtct  tcctggactg  ctgcaactac  atcacagagc  tgcggcggca  gcacgcgcgg
     2230        2240        2250        2260        2270        2280 gccagccacc  tgggcctggc  caggagtaac  ctggatgagg  acatcattgc  agaagagaac
     2290        2300        2310        2320        2330        2340 atcgtttccc  gaagtgagtt  cccagagagc  tggctgtgga  acgttgagga  cttgaaagag
     2350        2360        2370        2380        2390        2400 ccaccgaaaa  atggaatctc  tacgaagctc  atgaatatat  ttttgaaaga  ctccatcacc
     2410        2420        2430        2440        2450        2460 acgtgggaga  ttctggctgt  gagcatgtcg  gacaagaaag  ggatctgtgt  ggcagacccc
     2470        2480        2490        2500        2510        2520 ttcgaggtca  cagtaatgca  ggacttcttc  atcgacctgc  ggctacccta  ctctgttgtt
     2530        2540        2550        2560        2570        2580
```

FIG.2C

| | | | | | |
|---|---|---|---|---|---|
| cgaaacgagc | aggtggaaat | ccgagccgtt | ctctacaatt | accggcagaa | ccaagagctc |
| 2590 | 2600 | 2610 | 2620 | 2630 | 2640 |
| aaggtgaggg | tggaactact | ccacaatcca | gccttctgca | gcctggccac | caccaagagg |
| 2650 | 2660 | 2670 | 2680 | 2690 | 2700 |
| cgtcaccagc | agaccataac | catccccccc | aagtcctcgt | tgtccgttcc | atatgtcatc |
| 2710 | 2720 | 2730 | 2740 | 2750 | 2760 |
| gtgccgctaa | agaccggcct | gcaggaagtg | gaagtcaagg | ctgctgtcta | ccatcatttc |
| 2770 | 2780 | 2790 | 2800 | 2810 | 2820 |
| atcagtgacg | gtgtcaggaa | gtccctgaag | gtcgtgccgg | aaggaatcag | aatgaacaaa |
| 2830 | 2840 | 2850 | 2860 | 2870 | 2880 |
| actgtggctg | ttcgcaccct | ggatccagaa | cgcctgggcc | gtgaaggagt | gcagaaagag |
| 2890 | 2900 | 2910 | 2920 | 2930 | 2940 |
| gacatcccac | ctgcagacct | cagtgaccaa | gtcccggaca | ccgagtctga | gaccagaatt |
| 2950 | 2960 | 2970 | 2980 | 2990 | 3000 |
| ctcctgcaag | ggaccccagt | ggcccagatg | acagaggatg | ccgtcgacgc | ggaacggctg |
| 3010 | 3020 | 3030 | 3040 | 3050 | 3060 |
| aagcacctca | ttgtgacccc | ctcgggctgc | ggggaacaga | acatgatcgg | catgacgccc |
| 3070 | 3080 | 3090 | 3100 | 3110 | 3120 |
| acggtcatcg | ctgtgcatta | cctggatgaa | acggagcagt | gggagaagtt | cggcctagag |
| 3130 | 3140 | 3150 | 3160 | 3170 | 3180 |
| aagcggcagg | gggccttgga | gctcatcaag | aaggggtaca | cccagcagct | ggacttcaga |
| 3190 | 3200 | 3210 | 3220 | 3230 | 3240 |
| caacccagct | ctgcctttgc | ggccttcgtg | aaacgggcac | ccagcacctg | gctgaccgcc |
| 3250 | 3260 | 3270 | 3280 | 3290 | 3300 |
| tacgtggtca | aggtcttctc | tctggctgtc | aacctcatcg | ccatcgactc | ccaagtcctc |
| 3310 | 3320 | 3330 | 3340 | 3350 | 3360 |
| tgcggggctg | ttaaatggct | gatcctggag | aagcagaagc | ccgacggggt | cttccaggag |
| 3370 | 3380 | 3390 | 3400 | 3410 | 3420 |
| gatgcgcccg | tgatacacca | agaaatgatt | ggtggattac | ggaacaacaa | cgagaaagac |
| 3430 | 3440 | 3450 | 3460 | 3170 | 3480 |
| atggccctca | cggcctttgt | tctcatctcg | ctgcaggagg | ctaaagatat | ttgcgaggag |
| 3490 | 3500 | 3510 | 3520 | 3530 | 3540 |

FIG.2D

| | | | | | |
|---|---|---|---|---|---|
| caggtcaaca 3550 | gcctgccagg 3560 | cagcatcact 3570 | aaagcaggag 3580 | acttccttga 3590 | agccaactac 3600 |
| atgaacctac 3610 | agagatccta 3620 | cactgtggcc 3630 | attgctggct 3640 | atgctctggc 3650 | ccagatgggc 3660 |
| aggctgaagg 3670 | ggcctcttct 3680 | taacaaattt 3690 | ctgaccacag 3700 | ccaaagataa 3710 | gaaccgctgg 3720 |
| gaggaccctg 3730 | gtaagcagct 3740 | ctacaacgtg 3750 | gaggccacat 3760 | cctatgccct 3770 | cttggcccta 3780 |
| ctgcagctaa 3790 | aagactttga 3800 | ctttgtgcct 3810 | cccgtcgtgc 3820 | gttggctcaa 3830 | tgaacagaga 3840 |
| tactacggtg 3850 | gtggctatgg 3860 | ctctacccag 3870 | gccaccttca 3880 | tggtgttcca 3890 | agccttggct 3900 |
| caataccaaa 3910 | aggacgcccc 3920 | tgaccaccag 3930 | gaactgaacc 3940 | ttgatgtgtc 3950 | cctccaactg 3960 |
| cccagccgca 3970 | gctccaagat 3980 | cacccaccgt 3990 | atccactggg 4000 | aatctgccag 4010 | cctcctgcga 4020 |
| tcagaagaga 4030 | ccaaggaaaa 4040 | tgagggtttc 4050 | acagtcacag 4060 | ctgaaggaaa 4070 | aggccaaggc 4080 |
| accttgtcgg 4090 | tggtgacaat 4100 | gtaccatgct 4110 | aaggccaaag 4120 | atcaactcac 4130 | ctgtaataaa 4140 |
| ttcgacctca 4150 | aggtcaccat 4160 | aaaaccagca 4170 | ccggaaacag 4180 | aaaagaggcc 4190 | tcaggatgcc 4200 |
| aagaacacta 4210 | tgatccttga 4220 | gatctgtacc 4230 | aggtaccggg 4240 | gagaccagga 4250 | tgccactatg 4260 |
| tctatattgg 4270 | acatatccat 4280 | gatgactggc 4290 | tttgctccag 4300 | acacagatga 4310 | cctgaagcag 4320 |
| ctggccaatg 4330 | gtgttgacag 4340 | atacatctcc 4350 | aagtatgagc 4360 | tggacaaagc 4370 | cttctccgat 4380 |
| aggaacaccc 4390 | tcatcatcta 4400 | cctggacaag 4410 | gtctcacact 4420 | ctgaggatga 4430 | ctgtctagct 4440 |
| ttcaaagttc 4450 | accaatactt 4460 | taatgtagag 4470 | cttatccagc 4480 | ctggagcagt 4490 | caaggtctac 4500 |

FIG.2E

```
gcctattaca  acctggagga  aagctgtacc  cggttctacc  atccggaaaa  ggaggatgga
   4510        4520        4530        4540        4550        4560 aagctgaaca  agctctgccg  tgatgaactg  tgccgctgtg  ctgaggagaa  ttgcttcata
   4570        4580        4590        4600        4610        4620 caaaagtcgg  atgacaaggt  caccctggaa  gaacggctgg  acaaggcctg  tgagccagga
   4631        4640        4650        4660        4670        4680 gtggactatg  tgtacaagac  ccgactggtc  aaggtacagc  tgtccaatga  ctttgacgag
   4691        4700        4710        4720        4730        4740 tacatcatgg  ccattgagca  gaccatcaag  tcaggctcgg  atgaggtgca  ggttggacag
   4750        4760        4770        4780        4790        4800 cagcgcacgt  tcatcagccc  catcaagtgc  agagaagccc  tgaagctgga  ggagaagaaa
   4810        4820        4830        4840        4850        4860 cactacctca  tgtggggtct  ctcctccgat  ttctggggag  agaagcccaa  cctcagctac
   4870        4880        4890        4900        4910        4920 atcatcggga  aggacacttg  ggtggagcac  tggcctgagg  aggacgaatg  ccaagacgaa
   4930        4940        4950        4960        4970        4980 gagaaccaga  aacaatgcca  ggacctcggc  gccttcaccg  agagcatggt  tgtctttggg
   4990        5000        5010        5020        5030        5040 tgccccaact  gaccacaccc  ccattcc
   5050        5060
```

FIG.2F

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1663 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Met Gly Pro Thr Ser Gly Pro Ser Leu Leu Leu Leu Leu Thr His
1               5                  10                  15

Leu Pro Leu Ala Leu Gly Ser Pro Met Tyr Ser Ile Ile Thr Pro Asn
            20                  25                  30

Ile Leu Arg Leu Glu Ser Glu Glu Thr Met Val Leu Glu Ala His Asp
            35                  40                  45

Ala Gln Gly Asp Val Pro Val Thr Val Thr Val His Asp Phe Pro Gly
        50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
        130                 135                 140

Val Leu Tyr Arg Ile Phe Thr Val Asn His Lys Leu Leu Pro Val Gly
```

```
            145                 150                 155                 160
Arg Thr Val Met Val Asn Ile Glu Asn Pro Glu Gly Ile Pro Val Lys
                    165                 170                 175
Gln Asp Ser Leu Ser Ser Gln Asn Gln Leu Gly Val Leu Pro Leu Ser
                    180                 185                 190
Trp Asp Ile Pro Glu Leu Val Asn Met Gly Gln Trp Lys Ile Arg Ala
                    195                 200                 205
Tyr Tyr Glu Asn Ser Pro Gln Gln Val Phe Ser Thr Glu Phe Glu Val
                    210                 215                 220
Lys Glu Tyr Val Leu Pro Ser Phe Glu Val Ile Val Glu Pro Thr Glu
225                 230                 235                 240
Lys Phe Tyr Tyr Ile Tyr Asn Glu Lys Gly Leu Glu Val Thr Ile Thr
                    245                 250                 255
Ala Arg Phe Leu Tyr Gly Lys Lys Val Glu Gly Thr Ala Phe Val Ile
                    260                 265                 270
Phe Gly Ile Gln Asp Gly Glu Gln Arg Ile Ser Leu Pro Glu Ser Leu
                    275                 280                 285
Lys Arg Ile Pro Ile Glu Asp Gly Ser Gly Glu Val Val Leu Ser Arg
                    290                 295                 300
Lys Val Leu Asp Gly Val Gln Asn Pro Arg Ala Glu Asp Leu Val
305                 310                 315                 320
Gly Lys Ser Leu Tyr Val Ser Ala Thr Val Ile Leu His Ser Gly Ser
                    325                 330                 335
Asp Met Val Gln Ala Glu Arg Ser Gly Ile Pro Ile Val Thr Ser Pro
                    340                 345                 350
Tyr Gln Ile His Phe Thr Lys Thr Pro Lys Tyr Phe Lys Pro Gly Met
                    355                 360                 365
Pro Phe Asp Leu Met Val Phe Val Thr Asn Pro Asp Gly Ser Pro Ala
                    370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                    405                 410                 415
Gln Lys Pro Leu Ser Ile Thr Val Arg Thr Lys Lys Gln Glu Leu Ser
                    420                 425                 430
Glu Ala Glu Gln Ala Thr Arg Thr Met Gln Ala Leu Pro Tyr Ser Thr
                    435                 440                 445
Val Gly Asn Ser Asn Asn Tyr Leu His Leu Ser Val Leu Arg Thr Glu
                    450                 455                 460
Leu Arg Pro Gly Glu Thr Leu Asn Val Asn Phe Leu Leu Arg Met Asp
465                 470                 475                 480
Arg Ala His Glu Ala Lys Ile Arg Tyr Tyr Thr Tyr Leu Ile Met Asn
                    485                 490                 495
Lys Gly Arg Leu Leu Lys Ala Gly Arg Gln Val Arg Glu Pro Gly Gln
                    500                 505                 510
Asp Leu Val Val Leu Pro Leu Ser Ile Thr Thr Asp Phe Ile Pro Ser
                    515                 520                 525
Phe Arg Leu Val Ala Tyr Tyr Thr Leu Ile Gly Ala Ser Gly Gln Arg
                    530                 535                 540
Glu Val Val Ala Asp Ser Val Trp Val Asp Val Lys Asp Ser Cys Val
545                 550                 555                 560
Gly Ser Leu Val Val Lys Ser Gly Gln Ser Glu Asp Arg Gln Pro Val
                    565                 570                 575
```

-continued

```
Pro Gly Gln Gln Met Thr Leu Lys Ile Glu Gly Asp His Gly Ala Arg
            580                 585                 590
Val Val Leu Val Ala Val Asp Lys Gly Val Phe Val Leu Asn Lys Lys
        595                 600                 605
Asn Lys Leu Thr Gln Ser Lys Ile Trp Asp Val Val Glu Lys Ala Asp
    610                 615                 620
Ile Gly Cys Thr Pro Gly Ser Gly Lys Asp Tyr Ala Gly Val Phe Ser
625                 630                 635                 640
Asp Ala Gly Leu Thr Phe Thr Ser Ser Ser Gly Gln Gln Thr Ala Gln
                645                 650                 655
Arg Ala Glu Leu Gln Cys Pro Gln Pro Ala Arg Arg Arg Arg Ser
            660                 665                 670
Val Gln Leu Thr Glu Lys Arg Met Asp Lys Val Gly Lys Tyr Pro Lys
        675                 680                 685
Glu Leu Arg Lys Cys Cys Glu Asp Gly Met Arg Glu Asn Pro Met Arg
    690                 695                 700
Phe Ser Cys Gln Arg Arg Thr Arg Phe Ile Ser Leu Gly Glu Ala Cys
705                 710                 715                 720
Lys Lys Val Phe Leu Asp Cys Cys Asn Tyr Ile Thr Glu Leu Arg Arg
                725                 730                 735
Gln His Ala Arg Ala Ser His Leu Gly Leu Ala Arg Ser Asn Leu Asp
            740                 745                 750
Glu Asp Ile Ile Ala Glu Asn Ile Val Ser Arg Ser Glu Phe Pro
        755                 760                 765
Glu Ser Trp Leu Trp Asn Val Glu Asp Leu Lys Glu Pro Pro Lys Asn
    770                 775                 780
Gly Ile Ser Thr Lys Leu Met Asn Ile Phe Leu Lys Asp Ser Ile Thr
785                 790                 795                 800
Thr Trp Glu Ile Leu Ala Val Ser Met Ser Asp Lys Lys Gly Ile Cys
                805                 810                 815
    Val Ala Asp Pro Phe Glu Val Thr Val Met Gln Asp Phe Phe Ile Asp
            820                 825                 830
Leu Arg Leu Pro Tyr Ser Val Val Arg Asn Glu Gln Val Glu Ile Arg
            835                 840                 845
Ala Val Leu Tyr Asn Tyr Arg Gln Asn Gln Glu Leu Lys Val Arg Val
    850                 855                 860
Glu Leu Leu His Asn Pro Ala Phe Cys Ser Leu Ala Thr Thr Lys Arg
865                 870                 875                 880
Arg His Gln Gln Thr Ile Thr Ile Pro Pro Lys Ser Ser Leu Ser Val
                885                 890                 895
Pro Tyr Val Ile Val Pro Leu Lys Thr Gly Leu Gln Glu Val Glu Val
            900                 905                 910
Lys Ala Ala Val Tyr His His Phe Ile Ser Asp Gly Val Arg Lys Ser
        915                 920                 925
Leu Lys Val Val Pro Glu Gly Ile Arg Met Asn Lys Thr Val Ala Val
    930                 935                 940
Arg Thr Leu Asp Pro Glu Arg Leu Gly Arg Glu Gly Val Gln Lys Glu
945                 950                 955                 960
Asp Ile Pro Pro Ala Asp Leu Ser Asp Gln Val Pro Asp Thr Glu Ser
                965                 970                 975
Glu Thr Arg Ile Leu Leu Gln Gly Thr Pro Val Ala Gln Met Thr Glu
            980                 985                 990
```

```
Asp Ala Val Asp Ala Glu Arg Leu Lys His Leu Ile Val Thr Pro Ser
        995                 1000                1005
Gly Cys Gly Glu Gln Asn Met Ile Gly Met Thr Pro Thr Val Ile Ala
    1010                1015                1020
Val His Tyr Leu Asp Glu Thr Glu Gln Trp Glu Lys Phe Gly Leu Glu
1025                1030                1035                1040
Lys Arg Gln Gly Ala Leu Glu Leu Ile Lys Lys Gly Tyr Thr Gln Gln
                1045                1050                1055
Leu Ala Phe Arg Gln Pro Ser Ser Ala Phe Ala Ala Phe Val Lys Arg
            1060                1065                1070
Ala Pro Ser Thr Trp Leu Thr Ala Tyr Val Val Lys Val Phe Ser Leu
        1075                1080                1085
Ala Val Asn Leu Ile Ala Ile Asp Ser Gln Val Leu Cys Gly Ala Val
    1090                1095                1100
Lys Trp Leu Ile Leu Glu Lys Gln Lys Pro Asp Gly Val Phe Gln Glu
1105                1110                1115                1120
Asp Ala Pro Val Ile His Gln Glu Met Ile Gly Gly Leu Arg Asn Asn
                1125                1130                1135
Asn Glu Lys Asp Met Ala Leu Thr Ala Phe Val Leu Ile Ser Leu Gln
            1140                1145                1150
Glu Ala Lys Asp Ile Cys Glu Glu Gln Val Asn Ser Leu Pro Gly Ser
        1155                1160                1165
Ile Thr Lys Ala Gly Asp Phe Leu Glu Ala Asn Tyr Met Asn Leu Gln
    1170                1175                1180
 Arg Ser Tyr Thr Val Ala Ile Ala Gly Tyr Ala Leu Ala Gln Met Gly
1185                1190                1195                1200
Arg Leu Lys Gly Pro Leu Leu Asn Lys Phe Leu Thr Thr Ala Lys Asp
                1205                1210                1215
Lys Asn Arg Trp Glu Asp Pro Gly Lys Gln Leu Tyr Asn Val Glu Ala
            1220                1225                1230
Thr Ser Tyr Ala Leu Leu Ala Leu Leu Gln Leu Lys Asp Phe Asp Phe
        1235                1240                1245
Val Pro Pro Val Val Arg Trp Leu Asn Glu Gln Arg Tyr Tyr Gly Gly
    1250                1255                1260
Gly Tyr Gly Ser Thr Gln Ala Thr Phe Met Val Phe Gln Ala Leu Ala
1265                1270                1275                1280
Gln Tyr Gln Lys Asp Ala Pro Asp His Gln Glu Leu Asn Leu Asp Val
                1285                1290                1295
Ser Leu Gln Leu Pro Ser Arg Ser Ser Lys Ile Thr His Arg Ile His
            1300                1305                1310
Trp Glu Ser Ala Ser Leu Leu Arg Ser Glu Glu Thr Lys Glu Asn Glu
        1315                1320                1325
Gly Phe Thr Val Thr Ala Glu Gly Lys Gly Gln Gly Thr Leu Ser Val
    1330                1335                1340
Val Thr Met Tyr His Ala Lys Ala Lys Asp Gln Leu Thr Cys Asn Lys
1345                1350                1355                1360
Phe Asp Leu Lys Val Thr Ile Lys Pro Ala Pro Glu Thr Glu Lys Arg
                1365                1370                1375
Pro Gln Asp Ala Lys Asn Thr Met Ile Leu Glu Ile Cys Thr Arg Tyr
            1380                1385                1390
Arg Gly Asp Gln Asp Ala Thr Met Ser Ile Leu Asp Ile Ser Met Met
        1395                1400                1405
Thr Gly Phe Ala Pro Asp Thr Asp Asp Leu Lys Gln Leu Ala Asn Gly
```

```
                      1410            1415            1420
Val Asp Arg Tyr Ile Ser Lys Tyr Glu Leu Asp Lys Ala Phe Ser Asp
1425            1430            1435            1440

Arg Asn Thr Leu Ile Ile Tyr Leu Asp Lys Val Ser His Ser Glu Asp
            1445            1450            1455

Asp Cys Leu Ala Phe Lys Val His Gln Tyr Phe Asn Val Glu Leu Ile
            1460            1465            1470

Gln Pro Gly Ala Val Lys Val Tyr Ala Tyr Tyr Asn Leu Glu Glu Ser
            1475            1480            1485

Cys Thr Arg Phe Tyr His Pro Glu Lys Glu Asp Gly Lys Leu Asn Lys
            1490            1495            1500

Leu Cys Arg Asp Glu Leu Cys Arg Cys Ala Glu Glu Asn Cys Phe Ile
1505            1510            1515            1520

Gln Lys Ser Asp Asp Lys Val Thr Leu Glu Glu Arg Leu Asp Lys Ala
            1525            1530            1535

Cys Glu Pro Gly Val Asp Tyr Val Tyr Lys Thr Arg Leu Val Lys Val
            1540            1545            1550

Gln Leu Ser Asn Asp Phe Asp Glu Tyr Ile Met Ala Ile Glu Gln Thr
            1555            1560            1565

Ile Lys Ser Gly Ser Asp Glu Val Gln Val Gly Gln Gln Arg Thr Phe
            1570            1575            1580

Ile Ser Pro Ile Lys Cys Arg Glu Ala Leu Lys Leu Glu Glu Lys Lys
1585            1590            1595            1600

His Tyr Leu Met Trp Gly Leu Ser Ser Asp Phe Trp Gly Glu Lys Pro
                1605            1610            1615

Asn Leu Ser Tyr Ile Ile Gly Lys Asp Thr Trp Val Glu His Trp Pro
            1620            1625            1630

Glu Glu Asp Glu Cys Gln Asp Glu Glu Asn Gln Lys Gln Cys Gln Asp
            1635            1640            1645

Leu Gly Ala Phe Thr Glu Ser Met Val Val Phe Gly Cys Pro Asn
            1650            1655            1660

(2) INFORMATION FOR SEQ ID NO: 2:

(i) SEQUENCE CHARACTERISTICS:
        (A) LENGTH: 5056 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

CCTCTCCCTC TGTCCCTCTG TCCCTCTGAC CCTGCACTGT CCCAGCACCA TGGGACCCAC      60

CTCAGGTCCC AGCCTGCTGC TCCTGCTACT AACCCACCTC CCCCTGGCTC TGGGGAGTCC     120

CATGTACTCT ATCATCACCC CCAACATCTT GCGGCTGGAG AGCGAGGAGA CCATGGTGCT     180

GGAGGCCCAC GACGCGCAAG GGGATGTTCC AGTCACTGTT ACTGTCCACG ACTTCCCAGG     240

CAAAAAACTA GTGCTGTCCA GTGAGAAGAC TGTGCTGACC CCTGCCACCA ACCACATGGG     300

CAACGTCACC TTCACGATCC CAGCCAACAG GGAGTTCAAG TCAGAAAAGG GGCGCAACAA     360

GTTCGTGACC GTGCAGGCCA CCTTCGGGAC CCAAGTGGTG GAGAAGGTGG TGCTGGTCAG     420

CCTGCAGAGC GGGTACCTCT TCATCCCGAC AGACAAGACC ATCTACACCC CTGGCTCCAC     480

AGTTCTCTAT CGGATCTTCA CCGTCAACCA AAGCTGCTA CCCGTGGGCC GGACGGTCAT     540

GGTCAACATT GAGAACCCGG AAGGCATCCC GGTCAAGCAG GACTCCTTGT CTTCTCAGAA     600
```

```
CCAGCTTGGC GTCTTGCCCT TGTCTTGGGA CATTCCGGAA CTCGTCAACA TGGGCCAGTG    660
GAAGATCCGA GCCTACTATG AAAACTCACC ACAGCAGGTC TTCTCCACTG AGTTTGAGGT    720
GAAGGAGTAC GTGCTGCCCA GTTTCGAGGT CATAGTGGAG CCTACAGAGA AATTCTACTA    780
CATCTATAAC GAGAAGGGCC TGGAGGTCAC CATCACCGCC AGGTTCCTCT ACGGGAAGAA    840
AGTGGAGGGA ACTGCCTTTG TCATCTTCGG GATCCAGGAT GGCGAACAGA GGATTTCCCT    900
 GCCTGAATCC CTCAAGCGCA TTCCGATTGA GGATGGCTCG GGGGAGGTTG TGCTGAGCCG    960
GAAGGTACTG CTGGACGGGG TGCAGAACCC CCGAGCAGAA GACCTGGTGG GGAAGTCTTT   1020
GTACGTGTCT GCCACCGTCA TCTTGCACTC AGGCAGTGAC ATGGTGCAGG CAGAGCGCAG   1080
CGGGATCCCC ATCGTGACCT CTCCCTACCA GATCCACTTC ACCAAGACAC CCAAGTACTT   1140
CAAACCAGGA ATGCCCTTTG ACCTCATGGT GTTCGTGACG AACCCTGATG CTCTCCAGC    1200
CTACCGAGTC CCCGTGGCAG TCCAGGGCGA GGACACTGTG CAGTCTCTAA CCCAGGGAGA   1260
TGGCGTGGCC AAACTCAGCA TCAACACACA CCCCAGCCAG AAGCCCTTGA GCATCACGGT   1320
GCGCACGAAG AAGCAGGAGC TCTCGGAGGC AGAGCAGGCT ACCAGGACCA TGCAGGCTCT   1380
GCCCTACAGC ACCGTGGGCA ACTCCAACAA TTACCTGCAT CTCTCAGTGC TACGTACAGA   1440
GCTCAGACCC GGGGAGACCC TCAACGTCAA CTTCCTCCTG CGAATGGACC GCGCCCACGA   1500
GGCCAAGATC CGCTACTACA CCTACCTGAT CATGAACAAG GGCAGGCTGT TGAAGGCGGG   1560
ACGCCAGGTG CGAGAGCCCG GCCAGGACCT GGTGGTGCTG CCCCTGTCCA TCACCACCGA   1620
CTTCATCCCT TCCTTCCGCC TGGTGGCGTA CTACACGCTG ATCGGTGCCA GCGGCCAGAG   1680
GGAGGTGGTG GCCGACTCCG TGTGGGTGGA CGTCAAGGAC TCCTGCGTGG GCTCGCTGGT   1740
GGTAAAAAGC GGCCAGTCAG AAGACCGGCA GCCTGTACCT GGGCAGCAGA TGACCCTGAA   1800
GATAGAGGGT GACCACGGGG CCCGGGTGGT ACTGGTGGCC GTGGACAAGG GCGTGTTCGT   1860
GCTGAATAAG AAGAACAAAC TGACGCAGAG TAAGATCTGG GACGTGGTGG AGAAGGCAGA   1920
CATCGGCTGC ACCCCGGGCA GTGGGAAGGA TTACGCCGGT GTCTTCTCCG ACGCAGGGCT   1980
GACCTTCACG AGCAGCAGTG CCAGCAGAC CGCCCAGAGG GCAGAACTTC AGTGCCCGCA   2040
GCCAGCCGCC CGCCGACGCC GTTCCGTGCA GCTCACGGAG AAGCGAATGG ACAAAGTCGG   2100
CAAGTACCCC AAGGAGCTGC GCAAGTGCTG CGAGGACGGC ATGCGGGAGA ACCCCATGAG   2160
GTTCTCGTGC CAGCGCCGGA CCCGTTTCAT CTCCCTGGGC GAGGCGTGCA AGAAGGTCTT   2220
CCTGGACTGC TGCAACTACA TCACAGAGCT GCGGCGGCAG CACGCGCGGG CCAGCCACCT   2280
GGGCCTGGCC AGGAGTAACC TGGATGAGGA CATCATTGCA GAAGAGAACA TCGTTTCCCG   2340
AAGTGAGTTC CCAGAGAGCT GGCTGTGGAA CGTTGAGGAC TTGAAAGAGC CACCGAAAAA   2400
TGGAATCTCT ACGAAGCTCA TGAATATATT TTTGAAAGAC TCCATCACCA CGTGGGAGAT   2460
TCTGGCTGTG AGCATGTCGG ACAAGAAAGG GATCTGTGTG GCAGACCCCT TCGAGGTCAC   2520
AGTAATGCAG GACTTCTTCA TCGACCTGCG GCTACCCTAC TCTGTTGTTC GAAACGAGCA   2580
GGTGGAAATC CGAGCCGTTC TCTACAATTA CCGGCAGAAC CAAGAGCTCA GGTGAGGGT   2640
GGAACTACTC CACAATCCAG CCTTCTGCAG CCTGGCCACC ACCAAGAGGC GTCACCAGCA   2700
GACCATAACC ATCCCCCCCA GTCCTCGTT GTCCGTTCCA TATGTCATCG TGCCGCTAAA   2760
GACCGGCCTG CAGGAAGTGG AAGTCAAGGC TGCTGTCTAC CATCATTTCA TCAGTGACGG   2820
TGTCAGGAAG TCCCTGAAGG TCGTGCCGGA AGGAATCAGA ATGAACAAAA CTGTGGCTGT   2880
TCGCACCCTG GATCCAGAAC GCCTGGGCCG TGAAGGAGTG CAGAAAGAGG ACATCCCACC   2940
```

```
TGCAGACCTC AGTGACCAAG TCCCGGACAC CGAGTCTGAG ACCAGAATTC TCCTGCAAGG   3000

GACCCCAGTG GCCCAGATGA CAGAGGATGC CGTCGACGCG AACGGCTGA AGCACCTCAT   3060

TGTGACCCCC TCGGGCTGCG GGGAACAGAA CATGATCGGC ATGACGCCCA CGGTCATCGC   3120

TGTGCATTAC CTGGATGAAA CGGAGCAGTG GGAGAAGTTC GGCCTAGAGA AGCGGCAGGG   3180

GGCCTTGGAG CTCATCAAGA AGGGGTACAC CCAGCAGCTG GCCTTCAGAC AACCCAGCTC   3240

TGCCTTTGCG GCCTTCGTGA ACGGGCACC CAGCACCTGG CTGACCGCCT ACGTGGTCAA    3300

GGTCTTCTCT CTGGCTGTCA ACCTCATCGC CATCGACTCC CAAGTCCTCT GCGGGGCTGT   3360

TAAATGGCTG ATCCTGGAGA AGCAGAAGCC CGACGGGGTC TTCCAGGAGG ATGCGCCCGT   3420

GATACACCAA GAAATGATTG GTGGATTACG GAACAACAAC GAGAAAGACA TGGCCCTCAC   3480

GGCCTTTGTT CTCATCTCGC TGCAGGAGGC TAAAGATATT TGCGAGGAGC AGGTCAACAG   3540

CCTGCCAGGC AGCATCACTA AAGCAGGAGA CTTCCTTGAA GCCAACTACA TGAACCTACA   3600

GAGATCCTAC ACTGTGGCCA TTGCTGGCTA TGCTCTGGCC CAGATGGGCA GGCTGAAGGG   3660

GCCTCTTCTT AACAAATTTC TGACCACAGC CAAAGATAAG AACCGCTGGG AGGACCCTGG   3720

TAAGCAGCTC TACAACGTGG AGGCCACATC CTATGCCCTC TTGGCCCTAC TGCAGCTAAA   3780

AGACTTTGAC TTTGTGCCTC CCGTCGTGCG TTGGCTCAAT GAACAGAGAT ACTACGGTGG   3840

TGGCTATGGC TCTACCCAGG CCACCTTCAT GGTGTTCCAA GCCTTGGCTC AATACCAAAA   3900

GGACGCCCCT GACCACCAGG AACTGAACCT TGATGTGTCC CTCCAACTGC CCAGCCGCAG   3960

CTCCAAGATC ACCCACCGTA TCCACTGGGA ATCTGCCAGC CTCCTGCGAT CAGAAGAGAC   4020

CAAGGAAAAT GAGGGTTTCA CAGTCACAGC TGAAGGAAAA GGCCAAGGCA CCTTGTCGGT   4080

GGTGACAATG TACCATGCTA AGGCCAAAGA TCAACTCACC TGTAATAAAT TCGACCTCAA   4140

GGTCACCATA AAACCAGCAC CGGAAACAGA AAAGAGGCCT CAGGATGCCA AGAACACTAT   4200

GATCCTTGAG ATCTGTACCA GGTACCGGGG AGACCAGGAT GCCACTATGT CTATATTGGA   4260

CATATCCATG ATGACTGGCT TTGCTCCAGA CACAGATGAC CTGAAGCAGC TGGCCAATGG   4320

TGTTGACAGA TACATCTCCA AGTATGAGCT GGACAAAGCC TTCTCCGATA GGAACACCCT   4380

CATCATCTAC CTGGACAAGG TCTCACACTC TGAGGATGAC TGTCTAGCTT TCAAAGTTCA   4440

CCAATACTTT AATGTAGAGC TTATCCAGCC TGGAGCAGTC AAGGTCTACG CCTATTACAA   4500

CCTGGAGGAA AGCTGTACCC GGTTCTACCA TCCGGAAAAG GAGGATGGAA AGCTGAACAA   4560

GCTCTGCCGT GATGAACTGT GCCGCTGTGC TGAGGAGAAT TGCTTCATAC AAAAGTCGGA   4620

TGACAAGGTC ACCCTGGAAG AACGGCTGGA CAAGGCCTGT GAGCCAGGAG TGGACTATGT   4680

GTACAAGACC CGACTGGTCA AGGTTCAGCT GTCCAATGAC TTTGACGAGT ACATCATGGC   4740

CATTGAGCAG ACCATCAAGT CAGGCTCGGA TGAGGTGCAG GTTGGACAGC AGCGCACGTT   4800

CATCAGCCCC ATCAAGTGCA GAGAAGCCCT GAAGCTGGAG GAGAAGAAAC ACTACCTCAT   4860

GTGGGGTCTC TCCTCCGATT TCTGGGGAGA GAAGCCCAAC CTCAGCTACA TCATCGGGAA   4920

GGACACTTGG GTGGAGCACT GGCCTGAGGA GGACGAATGC CAAGACGAAG AGAACCAGAA   4980

ACAATGCCAG GACCTCGGCG CCTTCACCGA GAGCATGGTT GTCTTTGGGT GCCCCAACTG   5040

ACCACACCCC CATTCC                                                  5056
```

MODIFIED HUMAN C3 DNA SEQUENCES AND VECTORS

This application is a divisional of application Ser. No. 08/793,126, filed Feb. 7, 1997 now U.S. Pat. No. 5,849,297, which is a continuation of PCT/GB 95/02121 filed Sept. 8, 1995.

The present invention relates to novel modified proteins capable of forming stable C3 convertases, DNA sequences encoding such proteins and the use of such proteins as therapeutic agents, particularly for use in depleting levels of complement pathway proteins.

The complement system functions in the immune response of humans and other vertebrates, being of major importance in the effector functions such as phagocytosis, cytolysis and recruitment of cells that induce local inflammatory responses [15]. These properties are desirable for elimination of invading pathogens, such as bacteria, but undesirable when triggered to act against host tissues (e.g. in post-ischemic reperfusion injury [3]) or against foreign therapeutic material (e.g. hyperacute rejection of xenografts [7]). There have been attempts to abrogate these undesirable properties by exploiting derivatives of complement regulatory proteins whose normal function is to suppress complement activation [10, 18].

The complement system comprises proteins both on the surface of cells, (receptors and regulators) as well as in the fluid-phase (blood plasma and other extracellular environments). The critical step for the generation of responses is the proteolytic conversion of C3 to the fragments C3b and C3a. C3a is an anaphylatoxin that, like C5a, attracts mast cells to the site of challenge, resulting in local release of histamine, vasodilation and other inflammatory effects. The nascent C3b has an ability to bind to surfaces around its site of generation. This C3b then focuses attack by the cytolytic complement components (C5–C9). Surface-bound C3b, and its degradation products, also function as ligands for C3 receptors mediating, for example, phagocytosis [15]. There are two distinct pathways of complement activation that both result in conversion of C3 to C3b and subsequent responses. The classical pathway is commonly triggered by complexes of antibody with antigen, initiating an enzyme cascade involving the proteins Clq, Clr, Cls, C2 and C4. The alternative pathway depends on an activation loop involving C3 itself and requiring factors B and D.

Conversion of C3 to C3b (or C3i) produces a product that can combine with factor B, giving C3bB (or C3iB). These complexes are acted upon by factor D to generate C3bBb, which is a C3 convertase capable of cleaving more C3 to C3b, leading to more C3bBb and even more C3 conversion. Under certain circumstances the C3bBb complex is stabilised by association with the positive regulator properdin (P). However, this positive-feedback loop is normally limited to a slow tick-over by regulatory proteins, notably factor H and factor I.

Factor H (and structurally related cell-associated molecules) (i) displaces B and Bb from C3b, and (ii) acts as a cofactor for factor I which cleaves C3b into iC3b thereby preventing any recombination with factor B to form more C3 convertases. The pathway is "fired" into amplified generation of C3b in the presence of surfaces, such as many bacterial cell walls, that bind nascent C3b and impede its regulation by factors H and I. Nascent C3b is also able to bind to endogenous cells. Endogenous cell surfaces normally exposed to complement are therefore additionally protected by membrane-bound regulators such as MCP, DAF and CR1 acting in a similar manner to factor H.

There are a few rare naturally occurring conditions where the normal fluid-phase regulation cannot occur and spontaneous C3 conversion ultimately results in generalised depletion of C3 from the circulation:- (i) genetic deficiencies of factor H or I [13], (ii) the presence of antibodies (nephritic factors) that bind to C3bBb and impede dissociation [4], and (iii) contact with a protein in cobra venom, called cobra venom factor (CVF), that combines with factor B and forms a C3 convertase enzyme which does not contain C3b and is not affected by factors H and I [14]. These illustrate the normal physiological importance of down-regulation of complement in the absence of specific activation.

There are also circumstances where specific activation occurs, but is unwanted, particularly when it is directed against tissues of the host (e.g. tissue damaged by ischemia or surgery) or against foreign material deliberately given for therapeutic purposes (such as a xenograft, artificial organ or a dialysis membrane). The complement activation results in undesirable attack and further damage, so in these cases it would be beneficial to block or inhibit the activation and response.

Existing approaches to preventing complement-mediated damage have targeted the use of down-regulatory proteins (CR1, MCP, DAF and factors H and I) to inhibit complement activation. Complement inhibitors like factor I, factor H and soluble derivatives of the membrane-bound proteins CR1, DAF, MCP do suppress the fluid-phase amplification loop of the alternative pathway. Therefore there have been attempts to use these molecules, particularly CR1 (which seems to be the most potent) to reduce complement-mediated damage in models of physiological situations [10, 18].

Factor H is endogenously present in blood plasma in high concentrations (typically 0.3–0.5 mg/ml [15]), so even though increased levels of inhibitors do dampen-down fluid-phase reactions, their potency is weak so large amounts of purified proteins would have to be administered in vivo (e.g probably in excess of 5 mg/Kg body weight of soluble CR1). In addition, the alternative pathway is activated by surfaces where the effect of factor H is already impeded. While this does not necessarily concomitantly reduce the activities of other inhibitors, the same factors suggest that they are unlikely to be completely or universally effective.

Cobra Venom Factor(CVF) has the property of generating a stable C3 convertase which can be used experimentally to deplete complement in animals in vivo, and in other samples (e.g. human blood plasma) in vitro. CVF is potent (e.g. 40 $\mu$g/Kg can destroy the complement activity of a mouse [16]). However, there are disadvantages that make it unsuitable for therapeutic use in humans.

Firstly, it is obtained from cobra venom (a difficult source to obtain and dangerous to handle) and must therefore be carefully purified from the venom neurotoxins. There is also the obvious difficulty in obtaining supplies. This problem cannot readily be overcome by cloning and expressing the gene ex vivo, because there are post-translational modifications that occur in the snake (specific proteolytic processing) that may be difficult (or impossible) to reproduce in vitro.

In addition, the enzymes and digestion conditions required for this processing are currently unknown. Secondly, the protein is of foreign origin (to humans) and therefore immunogenic. This precludes its repeated therapeutic use, as would be required to decomplement a patient over many weeks (e.g. to allow xenograft survival).

Although CVF has some structural and functional homologies with human C3 [17], it also has major differences in both respects (e.g. chain structure, site of biosynthesis, insensitivity to complement regulators, formation of a stable C3 convertase). It is not derived from the cobra equivalent of C3 which is known, having been cloned and sequenced, and which in gross structure and function resembles human C3 more closely than does CVF [8].

CVF is a venom-specific product of an animal of great evolutionary distance from homo sapiens. It is therefore not practicable to use genetic manipulation to modify this protein into a product that can be used non-immunogenically in humans.

We have now devised an alternative strategy which relies on by-passing the physiological regulation and, instead of inhibiting complement activation, causes the system to be super-activated. This has two applications. Firstly, it can be used in vivo to activate complement until one or more components are exhausted, resulting in loss of ability to produce local responses to any subsequent challenge (such as a xenograft). Secondly, the unregulated super-activation can be deliberately localised to a particular target (e.g. a virus or a virally-infected cell) to increase the sensitivity of that target to complement-mediated destructive responses.

The term "regulators of complement activation" is used herein to include all proteins that act to inhibit amplification of C3 conversion, and is not intended to be restricted in meaning to those proteins whose genes are located in the RCA genetic locus. It does not however include "up-regulators" such as properdin. "C3 conversion" is defined as the proteolytic coversion of C3 into C3b and C3a, unless otherwise indicated, and "C3 convertase" (or simply "convertase") is defined as an enzyme (typically a complex of two or more protein components; for example C3bBb, C3iBb, CVFBb or C4b2a) that catalyses this reaction.

Thus, in a first aspect the invention provides a native complement pathway protein modified such that the protein is capable of forming a stable C3 convertase.

By "native" is meant naturally occurring, ie is obtainable in nature. Thus, the definition encompasses any naturally occurring complement pathway protein modified as defined above. It is not intended to be restricted to species specific proteins. In other words, a modified human protein could be used as a stable C3 convertase in other mammalian species, for example. Typically, modified complement pathway proteins from the same species will be used.

Modification of the C3 DNA coding sequence, for example using site directed mutagenesis, can produce a variant of C3 that is resistant to complement regulatory proteins while retaining positive functional properties (cleavage to C3b by C3 convertase) and features of structural integrity (correct chain structure, and presence of a thiolester bond). The invention described herein relates to genetically-modified forms of native complement proteins, for example human C3, whose C3b fragment acquires the property of being resistant to physiological complement regulation. Because of this resistance, these molecules can generate stabilised forms of the corresponding C3 convertase that produce amplified conversion of C3 to C3b, and later degradation products, in physiological environments (e.g. in vivo).

In a preferred embodiment the invention provides a modified human C3 protein which is resistant to cleavage by factor I.

This can be achieved by modifying residues of the protein at proteolytic sites.

A particularly preferred embodiment of the invention relates to a modified human C3 protein wherein the protein is modified by replacement of either Arg-1303, Arg-1320 or both by another amino acid. The other amino acid may be Tyrosine, Cystine, Tryptophan, Glutamine, Glutamic acid or Glycine. Arg-1303 is preferably replaced by Glutamic acid or Glycine (less preferably by Glutamine). Arg-1320 is preferably replaced by Glutamine.

Other stategies for producing suitable modified proteins of the invention include:

i) Reduced susceptibility to the inhibitory actions of factor H and related proteins (eg. MCP, DAF, CR1). For example, in human C3 residues 767–776 and 1209–1271 have been implicated in factor H binding [20,24], and substitution of one or more of these residues or other residues also associated with the action of these proteins, could reduce the binding of one or more of these regulatory proteins.

ii) Reduced rate of dissociation of C3bBb. Mutations can be introduced which would strengthen the interaction between C3b and Bb. This would result in both a reduction in spontaneous decomposition of the enzyme, and diminish the effectiveness of factor H(and related regulators) in displacing Bb from C3b.

These mutations are desirable to reduce the rates of both the spontaneous and the factor H-mediated decomposition of C3bBb. Even in the absence of factor H, the fluid phase C3bBb complex has a half-life of only about 10 mins at 37° C. in the presence of properdin [6].

iii) Human C3 residues 752–761 are implicated in binding factor B. It is a highly conserved region in C3, and a closely related seqence is found in C4. As C4 binds the factor B homolog C2, the strong similarity of this region between C3 and C4, together with its high conservation in C3, further supports its role in C3 as a factor B binding site. Thus, changes in this region could have effects on B affinity and on the stability of C3bBb.

iv) Resistance to other regulators of complement activation such as CR1, DAF and MCP would also be desirable. The mode of action of these regulators are all similar to factor H, so additional mutagenesis would not necessarily be required. Similarly, some pathogenic organisms express their own inhibitors of complement activation that are often structurally and functionally homologous to factor H (e.g. Vaccinia virus secretory peptide []) . These molecules protect the invaders against immune responses, and it would be advantageous to be able to attack them with targeted C3 convertase enzymes resistant to these defences.

v) Mutations that increase the stabilisation of the C3 convertase by properdin. The activity of properdin is to stabilise the C3bBb complex, retarding spontaneous and factor H-dependent dissociation. This stabilisation is ineffective in the fluid-phase, but seems to be more important in amplifying the process once it has already started on a suitable activating surface [5]. Increasing its activity (by increasing its affinity) may upset the balance in the fluid-phase, and thereby promote spontaneous C3 conversion. This should be particularly useful in combination with the other modifications described above.

vi) Mutations that prevent the C3bBb from possessing Cs convertase activity. When used to deplete active C3 from the circulation an undesirable side-effect could be the generation of large amounts of anaphylactic peptides. The most potent of these is C5a, which is cleaved from C5 by some C3 convertase enzymes. This reaction probably depends on the affinity of the convertase for another molecule of C3b [11], and so may be subject to suppression by mutations to the C3 that remove this interaction.

vii) Improved activity of the C3 convertase. The active site of the C3bBb C3 convertase enzyme resides in the Bb portion. The C3b component presumably functions to impose an active conformation on Bb and/or to bind and orientate the substrate to be acted upon by Bb. This is not known, but in either case there may be scope for enhancing the activity of the convertase through mutations in C3.

viii) Expression in a functional form. Wild-type C3 requires conversion to C3b before it can combine into a new C3 convertase complex. When used in vivo, a requirement for conversion to C3b (or C3i) would delay the action of the modified C3. It would therefore be desirable to either administer the protein in a form capable of immediate convertase formation, or to administer pre-formed convertase complexes. It is therefore advantageous to generate a functionally C3b-like reagent ex-vivo. This could be achieved in vitro (e.g. by proteolysis).

ix) Modifications to the native protein which serve to introduce new cleavage sites such that peptide regions required for factor B binding are retained but those required exclusively for factor H binding can be specifically removed. For example, sites can be introduced such that the C3b-like form of the modified C3 can be further cleaved into a form that still binds factor B but is less susceptible to inactivation by factors H and I.

x) Modifications in other regions which may affect the C3b interaction with factor B and/or factor H.

The invention is based on reversing the traditional approach by promoting C3 conversion to deplete C3 and thereby disable the system. An additional application of the invention is the potential to promote C3 conversion at a particular site, and thereby recruit the complement-dependent effector mechanisms to attack a specific target.

Therefore the ultimate effect will be to increase the amount of C3 conversion when the modified protein is administered into a physiological medium (e.g. blood) containing regulators of complement activation. This activity can then be used either to deplete that medium of native C3, or to localise the C3 conversion at a desired target.

The analogue of C3 whose C3b-fragment is resistant to the actions of factor I (e.g. the derivative described in example 1) would bind factor B, which would then be cleaved by factor D and eventually dissociate in an inactive form. In the absence of inactivation by factor I, the modified C3b would be able to repeatedly bind new molecules of factor B and thereby promote its inactivation. Therefore another potential application of modifications described in this invention would be the inactivation of the alternative pathway by consumption of factor B activity. An analogous approach could also be used to modify C4 to promote the consumption of C2, and thereby disable the classical pathway of complement activation.

The invention includes any other protease used in an analogous manner to the C3bBb enzyme which leads to cleavage of C3 to C3b, despite the presence of regulators of complement activation.

The invention also includes DNA sequences which code for a protein of the invention as well a s DNA constructs comprising such DNA sequences.

"DNA sequences" include all other nucleic acid sequences which, by virtue of the degeneracy of genetic code, also code for the given amino acid sequence or which are substantially homologous to this sequence. These sequences are thus also included within the scope of the invention.

Nucleic acid sequences which are "substantially homologous" are also within the scope of the present invention. "Substantial homology" may be assessed either at the nucleic acid level or at the amino acid level. At the nucleic acid level, sequences having substantial homology may be regarded as those which hybridise to the nucleic acid sequences of the invention under stringent conditions (for example, at 35 to 65° C. in a salt solution of about 0.9M). At the amino acid level, a protein sequence may be regarded as substantially homologous to another protein sequence if a significant number of the constituent amino acids exhibit homology. At least 55%, 60%, 70%, 80%, 90%, 95% or even 99%, in increasing order of preference, of the amino acids may be homologous.

As discussed above the proteins of the invention can be used to achieve localised complement activation effects. One way of ensuring this is to conjugate the protein to a moiety which will bind at the desired target. Thus, in another aspect the invention provides a conjugate comprising a protein of the invention linked to a specific binding moiety, for example a specific binding protein. An example of such a protein would be an antibody or an antigen binding fragment thereof.

The proteins of the invention are intended to be administered to a subject to elicit a desired therapeutic effect. To that end therefore the invention also provides:

a) A protein of the invention for use in therapy;

b) The use of a protein or a conjugate of the invention in the manufacture of a medicament for use in depleting levels of complement pathway protein, and in particular for use in preventing rejection of foreign matter;

c) A pharmaceutical formulation comprising one or more proteins or conjugates of the invention together with one or more pharmaceutically acceptable carriers and/or excipients; and d) A method of reducing complement pathway protein in a mammal which comprises administering to the mammal a protein of the invention, preferably in the form of a pharmaceutical formulation.

Pharmaceutical formulations may be presented in unit dose forms containing a predetermined amount of active ingredient per dose. Such a unit may contain as a minimum, for example, 1 mg of active ingredient, and preferably 2–3 mg. The upper limit which such a unit dose can contain will depend on many factors such as the condition being treated, the route of administration and the age, weight and condition of the patient as well as economic considerations. As an example a unit dose form can contain as much as 10 mg or even 100 mg of active ingredient.

The proteins of the invention could be used in vivo to disable the complement system. Circumstances where this may be desirable include the following:

(a) In order to prevent complement-mediated destruction or damage to a transplant, particularly a xenograft (material transplanted from a different species of animal), and especially a discordant xenograft (where the donor and recipient species are discordantly related) The recipient would be decomplemented prior to the operation and maintained in this state until the transplant had either been accommodated or been replaced by a more compatible organ.

The initial treatment could be made within several days before transplant a t ion. Additional decomplementation could be required at times of rejection crisis. The treatments may be accompanied by the use of anti-histamine reagents to control the general inflammatory responses (e.g. vasodilation) likely to result from the generation of C3a and/or C5a.

Decomplementation may also be beneficial in the use of artificial organs or tissues (e.g. artificial kidney dialysis membranes) which activate the complement system. As described above, the protein may be given either as the unactivated form, a functionally 3b-like form or a preformed active C3 convertase (like C3bBb). These may be administered by any route whereby the active convertase will encounter the circulating C3 (e.g. intravenously, subcutaneously etc.).

Another alternative would be an ex vivo treatment, for example by transfusing the circulation through a matrix bearing the active convertase. This could have the advantage of allowing anaphylactic peptides (C3a and C5a) and other low molecular weight inflammatory mediators (e.g. histamine and nitric oxide) to be removed (e.g. by dialysis) prior to the decomplemented blood (or plasma) being returned to the patient.

(b) To prevent complement-mediated damage resulting from major surgery. The patient would be decomplemented, as above, preferably before the operation (but if necessary afterwards) and kept in this state until the danger of additional internal injury due to complement-dependent immune attack had diminished.

(c) To minimise complement-mediated damage resulting from non-surgical injury. In these cases the decomplementation must be performed after the initial injury, but the formulations and methods of administration are likely to be otherwise similar to those described above. This may be particularly useful when the recovery involves reperfusion of an ischemic tissue by the circulation (e.g. myocardial ischemia, frostbite, burns etc.).

(d) To minimise complement-mediated damage resulting from antibody-antigen interactions. Complement-mediated defensive responses are particularly undesirable in autoimmune diseases which may include glomerulonephritis, haemolytic anaemia, myasthenia gravis and type II collagen-induced arthritis. Disabling the complement system during severe episodes of disease may alleviate the condition.

(e) To make a specific pathogenic target more susceptible to complement-mediated immune mechanisms. In this approach, the aim is not to use the super-active C3 convertase to produce generalised depletion of C3, but instead to use the convertase locally to concentrate the C3 conversion at a desired target. The target may be a pathogenic organism, such as a bacteria, virus or other parasite, or a deleterious host cell or tissue, such as a tumour cell or a virally-infected cell. The C3 convertase could be localised. to the target either by local administration (e.g. direct injection, possibly in a medium that retards its dispersion into the general circulation), or by combining with a targeting moiety, e.g. an antibody. Thus the modified protein could be linked to a specific immunoglobulin either by chemical cross-linking of the proteins, or by joining the DNA coding sequences and expressing (and purifying) the fusion protein (e.g. in the case of IgG, either the heavy or the light chain could be attached to C3 and co-expressed with C3, or both chains could be combined within one complete fusion polypeptide), or by incorporation of specific coding sequences (eg. for "leucine zipper"-like domains) to the DNA of both fusion partners (eg. modified C3 and specific antibody) such that the expressed products, when mixed together, self-associate to form stable conjugates. The fusion protein could then be administered locally or into the general circulation.

Liposomes (bearing the antibody on the surface with the modified protein either on the surface or inside the liposome) and/or virions (e.g. engineered to express the proteins on their surface) could also be used for co-delivery of antibody and modified protein. This strategy could be used directly, alone or in combination with other treatments, at any stage in the disease process. It may be particularly appropriate for use in eliminating any cancerous cells left in the circulation after surgical removal of a tumour. The antibody-modified protein conjugates could also be used ex vivo to eliminate pathogenic tissue. For example to kill leukaemic cells from an extracted bone-marrow and then returning the remaining healthy cells to the patient.

Alternatively lymphocytes that do not match the MHC types of the recipient could be eliminated from a bone marrow prior to transplantation. Also the modified protein could be linked to an antigen, and this combination could be used, either in vivo or ex vivo, to attack lymphocytes of undesirable reactivities (e.g. against transplant or self tissue).

The same technology would be applicable to treating other species, using either a human modified protein derivative, or a similar analogue tailor-made for that species.

Preferred features of each aspect of the invention are as for each each other aspect mutatis mutandis.

The invention will now be described by way of the following examples, which should not be construed as in any way limiting the invention. The examples refer to the accompanying drawings in which:

FIGS. 1A and 1B shows the predicted protein sequence of human C3 as encoded in PC3; (using the standard one letter amino acid code)

FIGS. 2A, 2B, 2C, 2D, 2E and 2F: show the cDNA sequence in PC3; (using the standard one letter deoxynucleotide code for the sense strand, written 5'—3').

FIG. 3: shows a visualisation of modified proteins of the invention.

Figure 4:
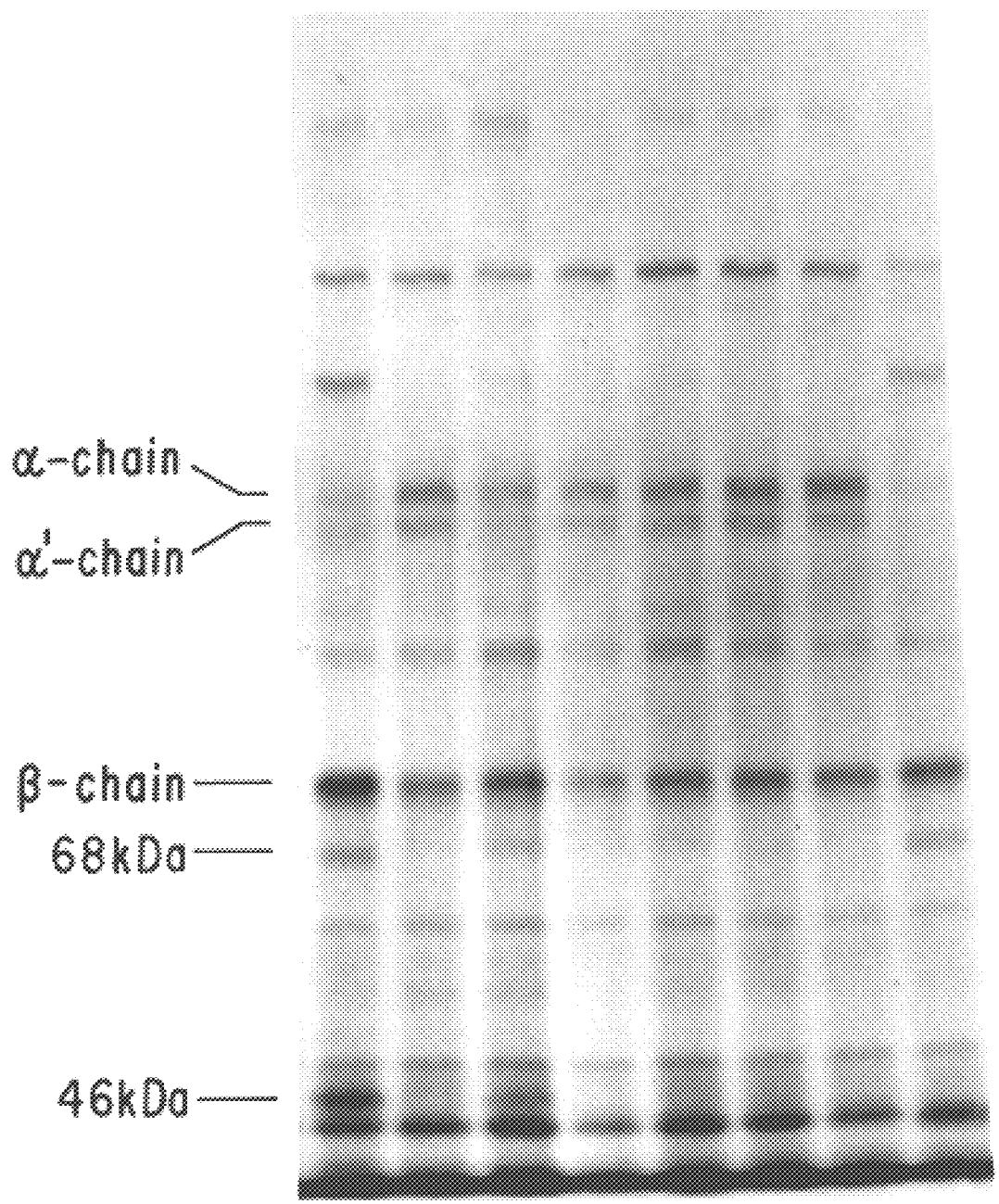

FIG. 4: shows the effect of various mutations to human C3 which replace Arg 1303 or Arg 1320 on factor I-medicated cleavage at these sites. N.B.
  1. [35S]-biosynthetically labelled samples.
  2. Reactions performed at normal ionic strength.
  3. Immunoprecipitated with anti-C3.
  4. SDS-PAGE under reducing conditions.
  5. Autoradiography.

Figure 5:
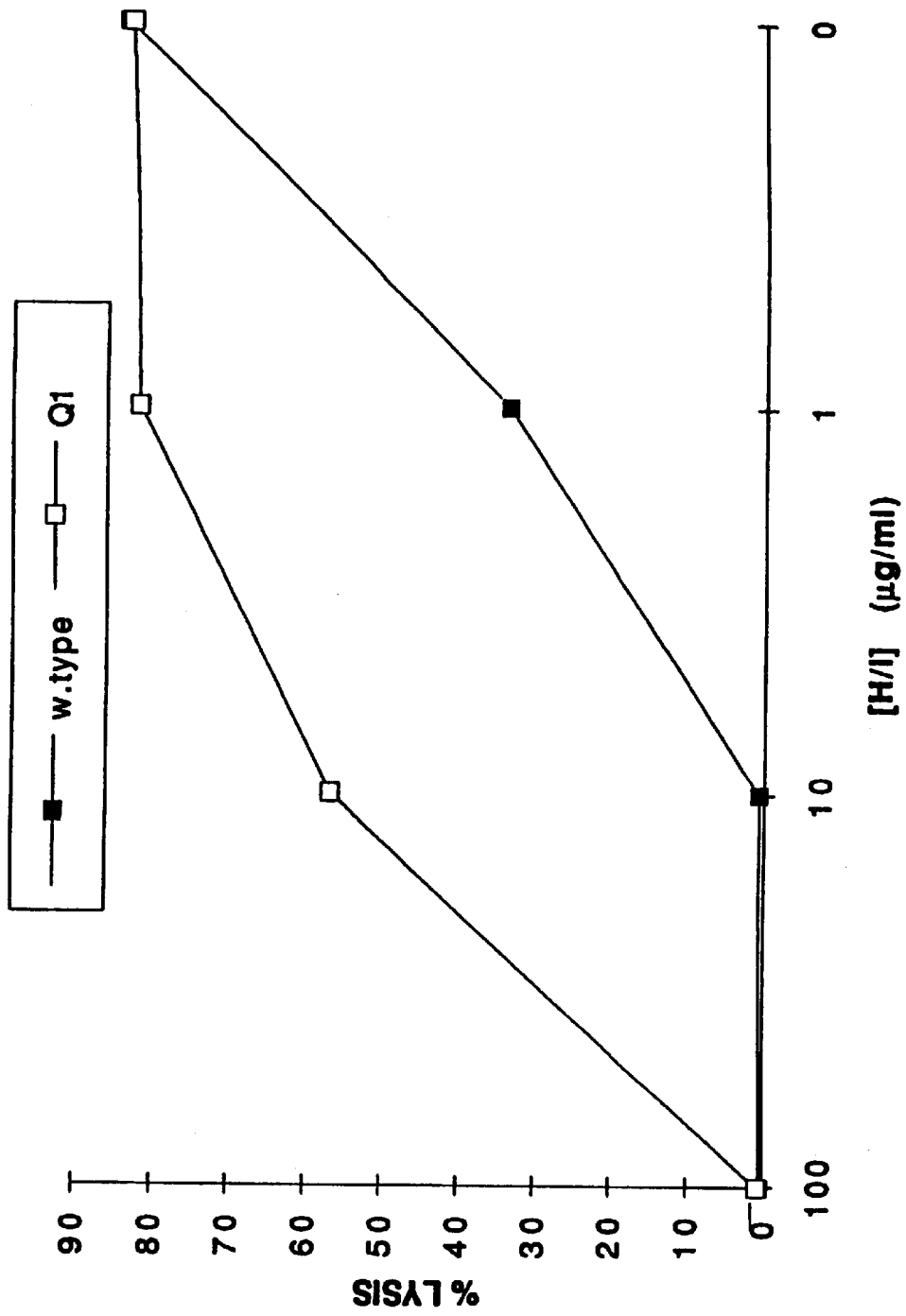

FIG. 5: shows enhanced resistance of human C3 incorporating the Arg 1303→Gln 1303 mutation to inactivation by factors I and H.

Figure 6:
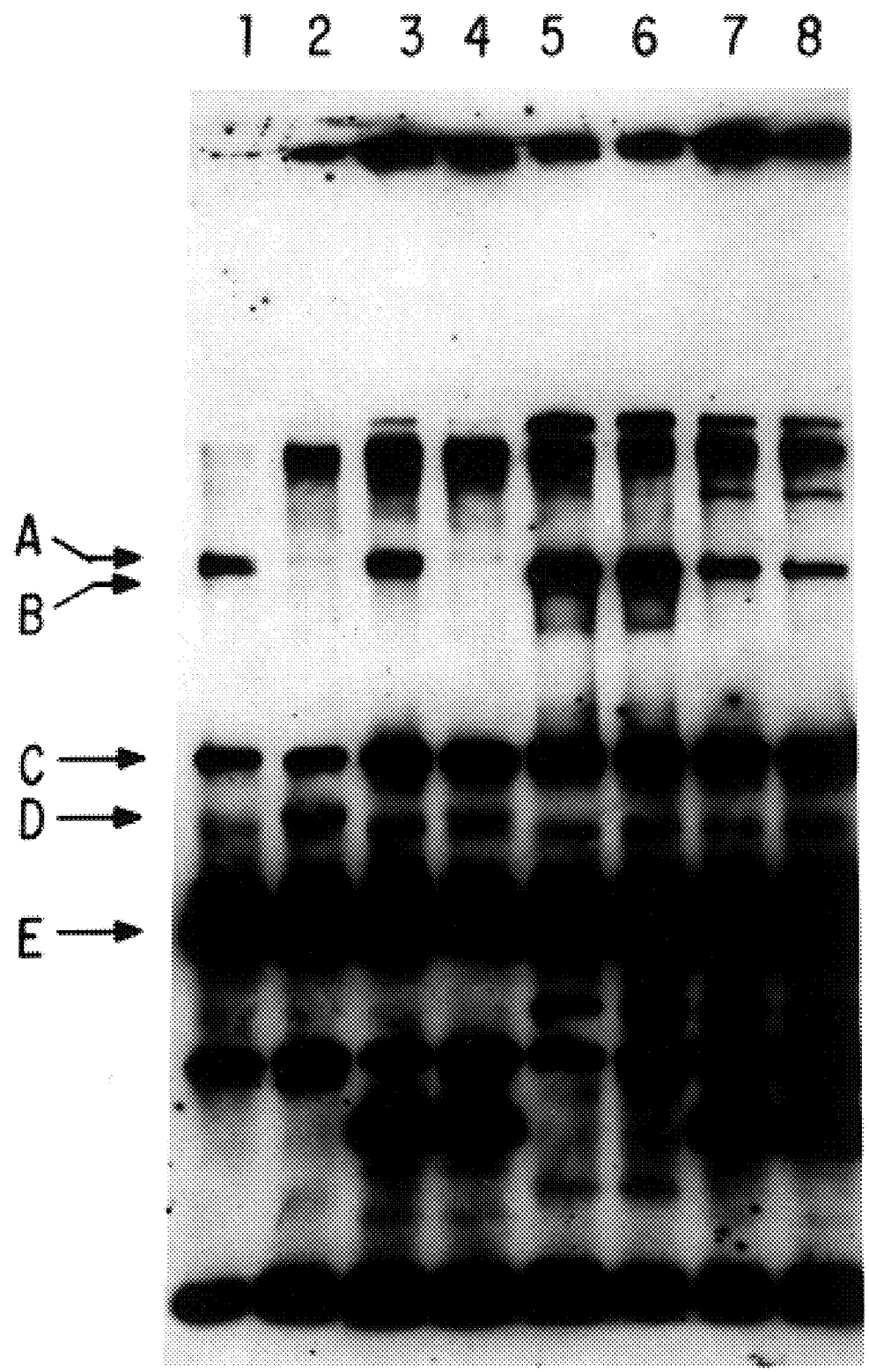

FIG. 6: shows an analysis of the cleavage of a C3 convertase mutated at amino acid residues 752–754 and 758–760.

This is a photograph of a Western Blot developed from a 7.5% polyacrylamide SDS-PAGE gel (reducing conditions), after electrophoretic transfer onto nitrocellulose, probing with a sheep anti-human C3 antibody, and development with horse-radish-peroxidase-coupled anti-sheep Immunoglobulin antibody and Enhance ChemiLuminescence (method and detection reagents from Amersham, U.K.) recorded on X-ray film. The cleavage reactions and detection procedure were performed as described in Example 4 with reference to the results shown in FIG. 3.

Key:
Tracks 1–4: wild-type C3 (expressed in COS cells)
Tracks 5–8: Mutant C3 (residues 752–754 changed
  to Gly-Ser-Gly and residues 758–760 also being
  changed to Gly-Ser-Gly) (expressed in COS cells)
Tracks 1,5: no addition
Tracks 2,6:+CVFBb
Tracks 3,7:+factors H+I
Tracks 4,8:+CVFBb+factors H+I The bands indicated by arrows are:

A: C3 alpha-chain

B: C3 alpha'-chain

C: C3 beta chain

D: 68 kDa cleavage product of C3 alpha'-chain

E: IgG heavy chain

Figure 7:
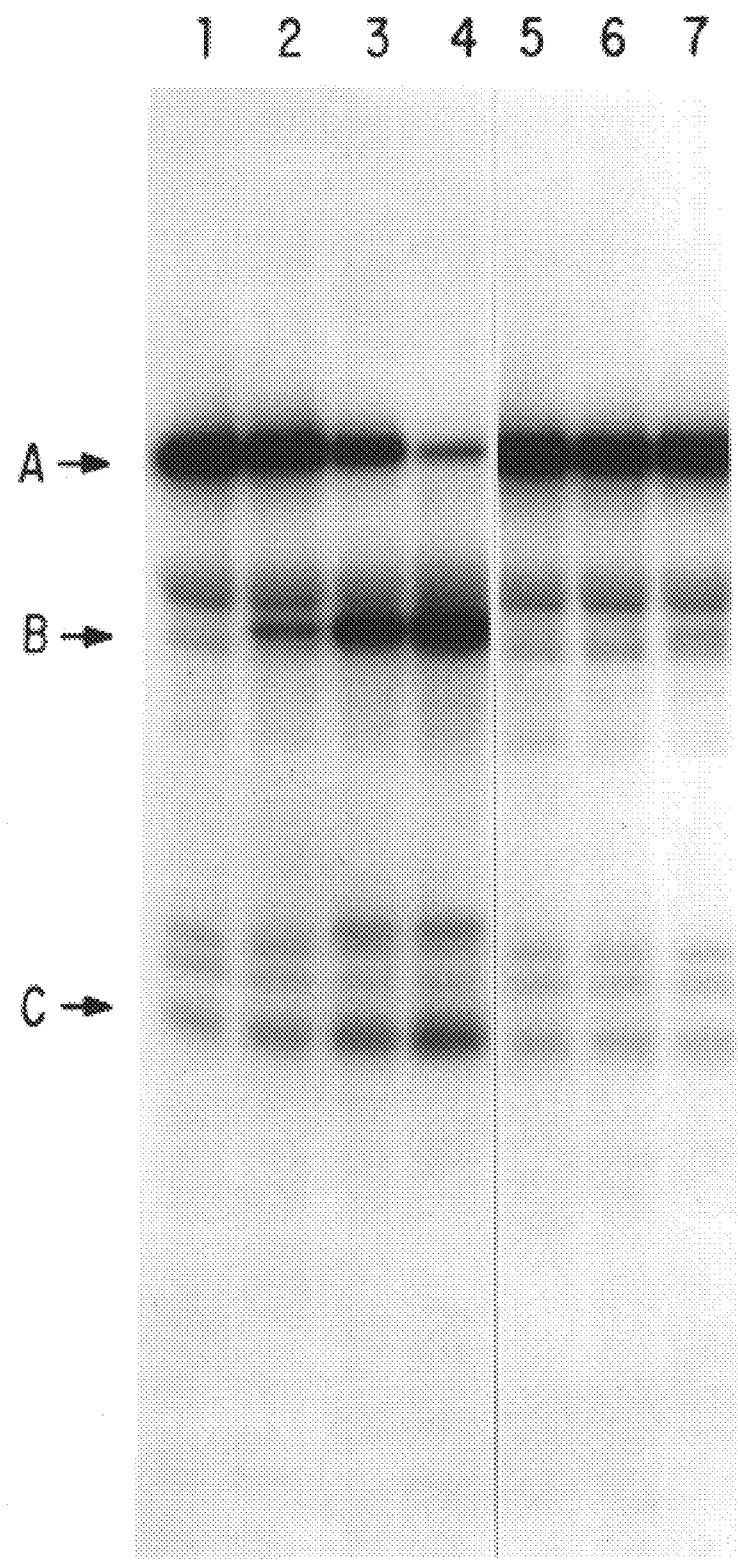

FIG. 7: shows an analysis of the cleavage of radiolabelled factor B by factor D, in the presence of wild-type and mutant C3's (C3i's)

A photograph of the autoradiograph of the SDS-PAGE gel is shown. All samples contained factor D and $^{125}$I-labelled factor B, and were incubated for 3 hours at 37° C.

The samples in the numbered tracks also included:

1. Buffer alone
2. 1/125 wild-type C3
3. 1/25 wild-type C3
4. 1/5 wild-type C3
5. 1/25 mutant C3 (residues 1427 Gon, 1431 Asp and 1433 Gln)
6 1/5 mutant C3
7. undiluted mutant C3

The bands indicated by arrows are:

A. Uncleaved $^{125}$I-labelled factor B (93 kDa)

B. 60 kDa cleavage product ("Bb")

C. 33 kDa cleavage product ("Ba")

Figure 8:
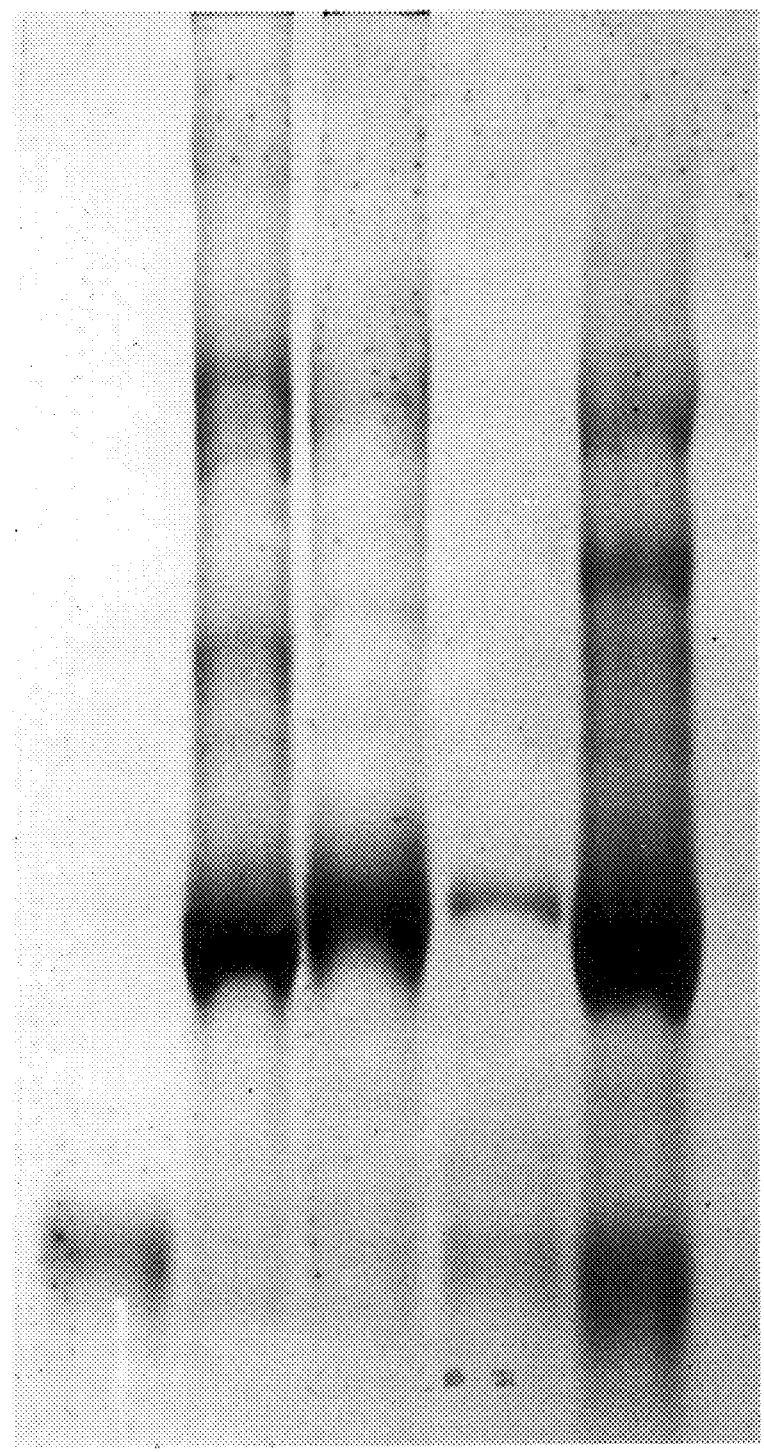

FIG. 8: shows an SDS-PAGE study illustrating the formation of a conjugate between C3i and IgG.

This is a Coomassie stain of a 4% acrylamide SDS-PAGE gel run under non-reducing conditions. The numbered tracks contain samples of:

1. PDP-IgG
2. C3i
3. PDP-IgG+C3i reaction mixture

Indicated by arrows are:

A. Probably C3i-IgG conjugate (350 kDa)

B. C3i (200 kDa)

C. IgG (150 kDa)

Figure 9:
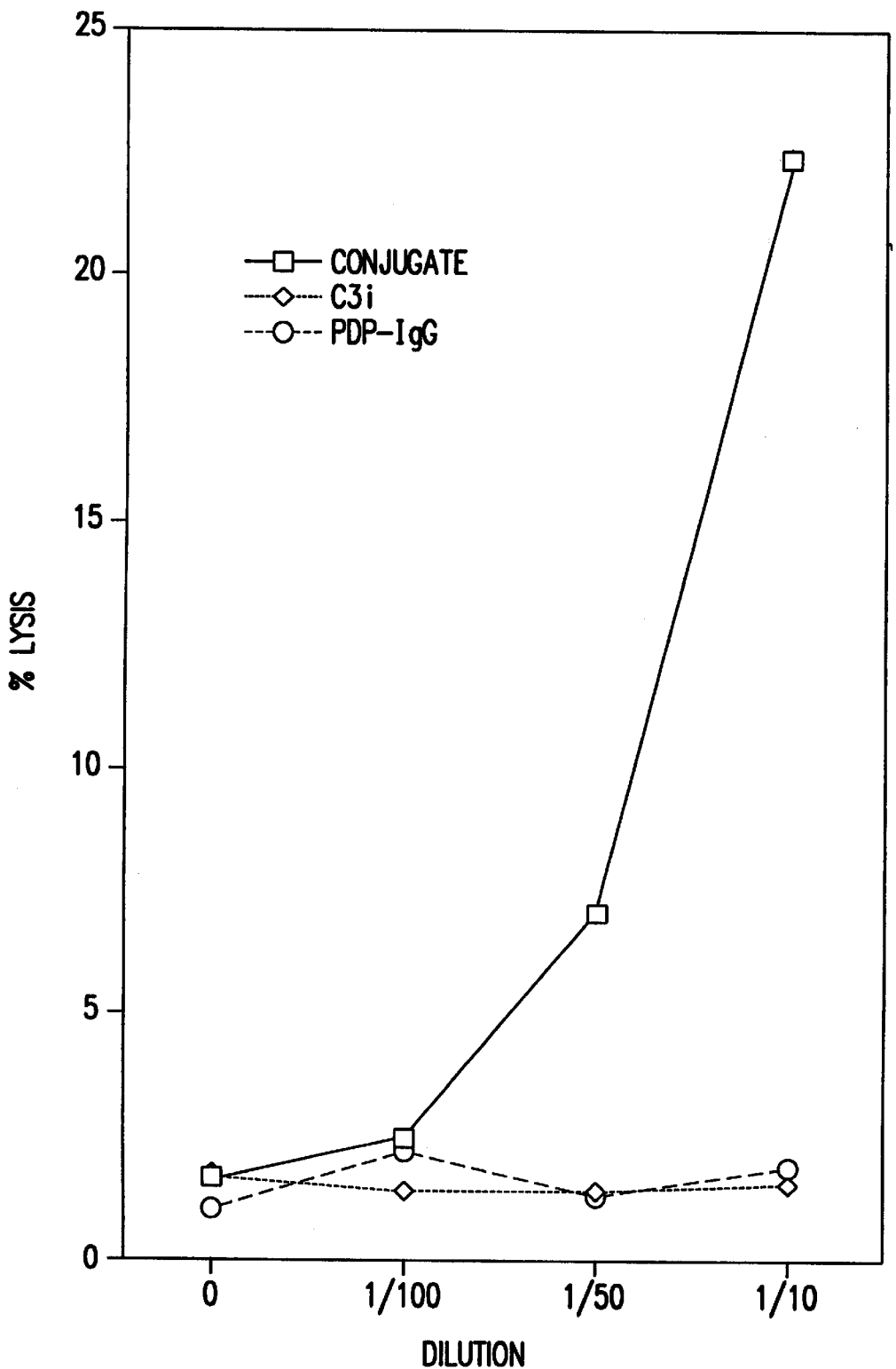

FIG. 9: demonstrates that conjugate targets C3 convertase activity against sheep erythrocytes. (This graph shows the % lysed sheep erythrocytes after coating with dilutions of either the C3i-IgG conjugate, PDP-IgG or C3i followed by washing, generation of C3 convertases with properdin and factors B and D, and finally development of lysis by NGPS in CFD/EDTA, as described in the methods. Only the conjugate produces lysis, and this lysis is dose dependent.)

The following standard methods and definitions are applicable to all the examples.

All complement components referred to are of human origin, unless otherwise specified, using standard terminology for all proteins and their derived fragments (e.g. as contained in reference [15]). In addition the term "C3i" refers to any molecular form of C3 without an intact thiolester bond, but retaining the C3a polypeptide on the alpha chain.

The human C3 cDNA and coding sequence are numbered as shown in FIG. 2, using the numbering used in the EMBL nucleotide data base (derived from reference [2]). The sequence shown is that of our construct ('PC3'), which lacks the first 11 nucleotides of the 5' untranslated region reported in reference [2], and hence the first base is numbered 12. The putative initiation codon is nucleotides number 61–63, the codon for the amino-terminal serine residue of the beta-chain is nucleotides 127–129, and the codon for the amino-terminal serine residue of the alpha-chain is nucleotides 2074–2076.

The protein sequence is numbered according to the precursor sequence as shown in FIG. 1, which is a predicted translation of the DNA sequence in Appendix 1 (amino acids 1–22 are expected to comprise a signal sequence that is removed during biosynthesis, and amino acids 668–671 are expected to be removed when the precursor is cleaved into the alpha and beta chains).

The following abbreviations have the following meanings; CVF cobra venom factor; ELISA, Enzyme-linked immunoadsorbant assay; *E. coli, Escherichia coli;* kb, kilobase; HSV-1, herpes simplex virus type 1; PBS, phosphate-buffered saline. COS-1 is a cell line derived from monkey kidney cells. The following are restriction endonucleases:- AflIII, DraI, DraIII, EcoRI, EcoRV, HindIII, NaeI, NheI, XbaI.

Standard Methods

Methods for standard molecular biological procedures such as plasmid isolations, agarose gel electrophoresis, and DNA ligations can be found in reference [21]. Double stranded DNA was sequenced using the 'Sequenase version 2.0' kit supplied by 'United States Biochemicals'. C3 expression was measured by an ELISA assay using plastic plates pre-coated with affinity-purified polyclonal sheep anti-human C3 to which samples of culture supernatant were added. Bound C3 was detected with a monoclonal rat antibody to C3 conjugated to alkaline phosphatase, and the chromogenic substrate, p-nitrophenol phosphate. Assays were calibrated with purified human plasma C3.

Methods for purification of complement proteins and CVF, and for the preparation of affinity purified anti-C3 antibodies usedin the analysis can be found in reference [28]. Equivalent reagents can also be purchased from Sigma chemical company LTD.

C3 cDNA Coding Sequence

Our C3 cDNA coding sequence was constructed from two segments isolated from a random-primed human liver cDNA library carried in the vector pGEM4 (Promega) Five oligodeoxynucleotides, corresponding to known segments in the human C3 coding sequence, were radiolabeled with T4 polynucleotide kinase and [γ-32P]·ATP and used to probe filter transfers of the library from agarose plates. Two clones containing inserts of approximately 4 kb were isolated. Restriction endonuclease digestion, hybridisation to specific oligodeoxynucleotide probes and partial sequence analysis demonstrated that one of these ('A13') included the 5'-end of the 5.1 kb message, whereas the other ('B44') extended to the 3'-end.

These inserts therefore overlapped by approximately 3 kb, including a unique EcoRI restriction enzyme site. The incomplete 5' section of A13 was cut out with EcoRI and NheI, and replaced with the complete segment isolated from B44 by digestion with EcoRI and XbaI. Both pieces were purified by gel electrophoresis in low-melting point agarose before ligating together with T4 DNA ligase to produce a vector ('PGC3') containing 5.1 kb of DNA encoding the entire C3 precursor protein.

Linker sequences 5' to the C3 coding region contained two ATG's which are potential false translation start sites. These were therefore removed by gapped-plasmid mutagenesis, as described in the method of example 1, using an oligodeoxynucleotide PL-ATC-3 (tagggagacc ggaagcttgc cctctccctc tgtccctctg t) that deleted approximately 50 base pairs of linker/adaptor DNA, without altering the C3 coding sequence. This mutated vector, 7.7 kb containing 5.1 kb of C3 cDNA sequence plus 2.6 kb of sequence from the PGEM4 vector (Pronega) is referred to as PC3.

The C3 coding region of the PGC3 plasmid was completely sequenced and revealed only four differences from a previously published human C3 ("S" allele) cDNA sequence [2].

(i) the changes C2481→G, and C2805→T do not alter the coding;

(ii) T1001→C encodes the previously described HAV 4-1-(Leucine314→Proline) polymorphic form [20]; and (iii) G2716→A encodes Valine886→Isoleucine, that has not been previously reported in human C3, although Ile is found in this position in mouse and rat C3.

Our sequence includes start and stop codons, with a complete signal sequence and should, therefore, encode functional C3.

Levels of up to 1.7 µg/ml expressed wild type C3 in culture supernatants of COS-1 cells (transfected using lipofectamine and the pcDNA3 (Invitrogen) expression vector) have been detected by ELISA. No detectable C3 was produced by cells transfected with pcDNA3 vector alone. Furthermore, analysis of the expressed product by cleavage reactions followed by immunoprecipitation, SDS-PAGE and immunoblotting demonstrated that:

(i) the primary translation product had been correctly processed into the mature two-chain form;

(ii) this product was, like native C3, cleavable to C3b by C3 convertase (CVFBb); and (iii) the expressed protein was, like native C3, not cleavable by factor H plus I, but became cleavable after conversion to C3b by C3 convertase enzyme. This confirms that our starting plasmid can be translated into functional C3.

For an alternative description of a construction and expression of a C3 coding sequence see reference [25].

EXAMPLE 1

Production of C3 that has the arginine residues at both factor I cleavage sites (amino acid positions 1303 and 1320) converted to glutamine residues to prevent cleavage of the C3b fragment by factor I.

a) Mutagenesis

Mutagenic oligodeoxynucleotides used were QRI1 (caactgcccagccaaagctccaagatcacc), QRI2 (gccagcctcctgcaatcagaagagaccaag), and AFL4149 (taataaattcgaccttaaggtcaccataaaac), as well as the corresponding antisense oligodeoxynucleotides QRI1n (ggtgatcttggagctttggctgggcagttg), QRI2n (cttggtctcttctgattgcaggaggctggc) and AFL4149n (gttttatggtgaccttaaggtcgaatttatta).

QRI1 and QRI1n specify the replacement of arginine for glutamine at the factor I cleavage site at amino acid residue 1303 in the C3 precursor sequence (by changing G3968C3969 to AA in the cDNA sequence), and QRI2 and QRI2n effect the same substitution at the factor cleavage site at amino acid residue 1320 (by changing nucleotide G4019 to A).

AFL4149 and AFL4149n introduce a cleavage site for the restriction endonuclease AflII at position 4149 in the cDNA sequence (by changing C4149 to T) without altering the encoded amino acid sequence. These two primers were used as markers, allowing successful mutagenesis to be identified on the basis of cleavage of the DNA product by AflII.

Mutagenesis was effected using the 'gapped' plasmid method. A batch of PGC3 ('UPGC3'), enriched in uridine in place of thymidine, was prepared by growth in E. Coli strain CJ236 in the presence of 0.25 µg/ml uridine. This plasmid was digested with SmaI and the 7.2 kb product ('US1') agarose gel purified to remove a 0.5 kb fragment from the C3 sequence (residues 1463–1947). The other component of the gapped plasmid ('DN2') was prepared by digesting PGC3 with DraIII plus NaeI and purifying the 5.1 kb piece twice by agarose gel electrophoresis. 200 ng DN2 was mixed with approximately 500 ng US1 in 50 µl H2O, heated to 100° C. and cooled slowly to below 50° C., before adding 20 µl to 25 µl of 2XT7 buffer (100 mM Tris/HCl/pH 7.4/14 mM MgCl2, 100 mM NaCl, 2 mM dithiothreitol, and 1 mM each of ATP, dATP, dCTP, dTTP and dGTP) plus 10 nmol of each 5'-phosphorylated mutagenic primer (one reaction used QRI1, QRI2 plus AFL4149, another reaction used QRI1n, QRI2n plus AFL4149n). The mixtures were reheated to 70° C. for 5 min and cooled slowly (over 30–60 min) to 20° C. At 0° C., 10 units of T7 DNA polymerase plus 80 units T4 DNA ligase are added. The mixture (total volume 50 µl) was incubated first at 0° C., for 5 min, then at room temperature for 5 min, and finally at 37° C. for 3 hours. 1 µl of each mixture was used to transform 100 µl supercompetent XL1 E. Coli (Stratagene) according to the manufacturer's instructions.

Ampicillin resistant colonies were screened for AflII cleavage, and successful mutants were grown up in 100 ml cultures from which the plasmids were isolated and sequenced (using a sequencing primer C3pa-3876, cttcatggtgttccaagcct, matching nucleotides 3876–3895 of C3 cDNA) to characterise mutations at the factor I cleavage sites.

For an alternative protocol for "gapped plasmid" mutagenesis see references [26,27].

b) Transfer of mutant DNA to eukaryotic expression vector

The C3 coding fragments from mutant plasmids were excised is by double digestion with HindIII and NaeI. DraI was also included to incapacitate the residual plasmid. The C3 coding sequence was agarose gel purified and ligated into pcDNA3 vector (Invitrogen) that had been linearised with HindIII and EcoRV enzymes and dephosphorylated with calf intestinal phosphorylase. Ligation mixtures were used to transform supercompetent XL1 E. coli, which were then plated onto culture plates containing ampicillin.

A random selection (three or four) of ampicillin resistant colonies were grown up in 2–3 ml cultures and small scale isolation of the plasmid DNA. The plasmids containing the correct insert were identified by digestion of the plasmid DNA with restriction endonucleases EcoRI, HindIII and AflII. The corresponding colonies grown up in 100 ml cultures and the plasmids purified by the standard procedure. These mutants were originally constructed from PGC3 and so retained the two ATG's 5' to the coding region. This region (plus the 5' 3 kb of the C3 coding sequence) was therefore excised with HindIII plus EcoRI and replaced by ligation of the same segment cut out of PC3. These reconstructed vectors were prepared by the standard procedure and used for transfection of COS cells.

c) Expression of Wild-type and Mutant C3's

Mutants and wild-type C3 were transiently expressed from plasmids transfected into COS-1 cells using lipofectamine® (GIBCO) according to the manufacturer's instructions. Typically, 1–1.5×10$^5$ cells per well of a standard 6 well culture plate were transfected with 2–4 µg of plasmid using 9µl of lipofectamine reagent. Supernatants were assayed for C3 secretion, and typical yields of 0.3–1.7 µg per ml supernatant were obtained 3–6 days after transfection.

RESULTS a) Generation of Mutants

The following mutants, named according to the mutagenic oligodeoxynucleotide sequences that have been incorporated, have so far been isolated (i) 3 mutants with both QRI1 and QRI2 mutations plus AFL4149: C3M-26, C3M-58 and C3M-61;

(ii) 1 mutant with QRI1 and QRI2 but without AFL4149: C3M-8; and (iii) 1 mutant with QRI2 and AFL4149, but without QRI1: C3M-51 (used in example 3)

b) Validation that Functional Effects were Due to the Mutations Specifically Introduced at the Factor I Cleavage Sites Sequencing has confirmed the absence of other alterations in 178–350 bases around the mutated region of each mutant. The sequence of one mutant produced by this procedure, C3M-51 (see example 3), has been analysed throughout the entire 'gap' (bases 2463–5067) used in mutagenesis, and no other deviations from the wild-type sequence were found.

Furthermore, representative sequencing of a total of 2922 bases from all mutants have not revealed any single point mutations that could have been caused by polymerase-mediated errors. The expressed mutants all displayed the two-chain structure and cleavage by C3 convertases characteristic of native C3. In summary, the mutants used are unlikely to contain any unwanted changes although they have not been completely re-sequenced.

EXAMPLE 2

Production of C3 that has the arginine residue at one factor I cleavage site (amino acid position 1303) converted to a glutamine residue The procedure of Example 1 was followed except that only mutagenic oligodeoxynucleotides AFL4149 plus QRI1 or AFL4149n plus QRI1n (i.e. no QRI2 or QRI2n), were used in mutagenesis.

RESULTS a) Mutants Obtained 2 mutants with QRI1 and AFL4149 but without QRI2 were isolated: C3M-I23,27. The mutant C3M-I23 was expressed, as described in Example 1.

This protein was cleavable by CVFBb. The C3b-like product was relatively (compared to the wild-type) resistant to cleavage at position 1303 by factors I and H, but could still be cleaved at position 1320. This C3b derivative is therefore partially resistant to factor I.

EXAMPLE 3

Production of C3 that has the arginine residue at one factor I cleavage site (amino acid position 1320) converted to a glutamine residue The procedure of Example 1 was followed except that only mutagenic oligodeoxynucleotides AFL4149 plus QRI2 or AFL4149n plus QRI2n (i.e. no QRI1 or QRI1n), were used in mutagenesis. In addition, the method used in example 1 also yielded one mutant with QRI2 and AFL4149, but without QRI1.

RESULTS a) Mutants Obtained 3 mutants with QRI2 and AFL4149 but without QRI1 were isolated:-C3M-51, C3M-Q2, C3M-Q13. The mutant C3M-51 was expressed, as described in Example 1. This protein was cleavable by CVFBb. The C3b-like product was not readily cleaved at position 1320 by factors I and H, but it could still be cleaved at position 1303. This C3b derivative is therefore partially resistant to factor I.

EXAMPLE 4

Analysis of the functional effects of mutations.

Supernatants (100–400 $\mu$l) from transfected COS cells were incubated at 37° C. for 2 h with:

COS cells were transfected with pCDNA3 carrying inserts of:

1) the unmutated C3 sequence;
2) mutant C3M-I 23 (encoding $Arg^{1303} \rightarrow Gln$)
3) mutant C3M-26 (encoding $Arg^{1303} \rightarrow Gln$, $Arg^{1320} \rightarrow Gln$); and
4) mutant C3M-51 (encoding $Arg^{1320} \rightarrow Gln$).

200 $\mu$l of the culture supernatants, taken 3 days after transfection, were pretreated with 2 mm phenylmethane-sulphonyl fluoride (0°, 15 min) and then incubated at 37° C. for 2 hours with the following:

A) no addition;
1) preformed C3 convertase, CVFBb (10 $\mu$l from 200$\mu$l containing 6.6 $\mu$g CVF, 100 $\mu$g factor B and 1.4 $\mu$g factor D in phosphate-buffered saline (PBS) containing 10 mM $MgCl_2$, preincubated at 37° C., 15 mins);
C) factors H (5 $\mu$g) and I (1 $\mu$g); and
D) CVFBB plus factors H and I.

These were then immunoprecipitated by adding 0.6 $\mu$g affinity-purified sheep anti-human C3 immunoglobulin at room temperature and after 1 hour adding 20 $\mu$l a 5% suspension of washed formalin-fixed Group C. Streptococcus sp. cells (protein G) (Sigma). After 45 min at room temperature the particles were washed once in PBS, 5 mM $NaN_3$, and once in 20 mM Tris/HCl, 137 mM NaCl, 0.1%: (v/v) Tween 20, pH 7.6 before eluting in 1% SDS/2% 2-mercaptoethanol (90–100° C., 5 min). These eluates were separated by SDS-PAGE, electroblotted onto nitrocellulose and the C3 bands detected by probing with affinity-purified sheep anti-human C3 immunoglobulin followed by horse radish peroxidase-coupled donkey anti-sheep immunoglobulin (Sigma) and detection using the "Enhanced Chemiluminescence" substrates supplied by Amersham. A photograph of a 2 minute exposure to X-ray film is shown. The visible C3-derived bands are indicated by labelled arrows, and the individual samples (1–4, A–D) are those just described. (The prominent band of about 50 kDa (between the 46 and 68 kDa bands) present in all samples is the heavy chain of the IgG used in the immunoprecipitation and detected by the horse radish peroxidase-coupled donkey anti-sheep immunoglobulin.).

RESULTS (see FIG. 3)

1. All the untreated samples (1-A, 2-A, 3-A, 4-A) contain bands of the correct migration for alpha and beta chains of C3, indicating that all the mutants are expressed, and post-translationally processed correctly. The presence of 43 or 46 kDa bands in these samples indicates the presence of some factor H+factor I-like activity in the culture medium. Spontaneous hydrolysis of C3 during the 3 day biosynthetic period produces C3i which is cleaved by this activity. In the unmutated C3 this generates bands of 43 kDa and 75 kDa (the 75 kDa band is invisible because (i) it is hidden by the 75 kDa beta chain, and (ii) the antibody used to develop the western blot has very little activity towards this portion of the C3 alpha chain: its presence was subsequently confirmed by reprobing with a rat monoclonal antibody, "Clone-3", that is specific for this region) The addition o f factors H and I without CVFBb (1-C, 2-C, 3-C, 4-C), did not cleave the remaining C3 indicating that this represented active C3 (thiolester intact).

2. The unmutated C3 (1) is cleaved by CVFBb and the C3b product is further cleaved by endogenous enzymes in 1-B or added factors H and I in 1-D. The 43 kDa band indicates cleavage at $Arg^{1320}$ and the 68 kDa band (visible in longer exposures) indicates cleavage at $Arg^{1303}$.

3. The mutant C3M-I23 (Arg$^{1303}$→Gln) was cleavable by cVFBb and th e product was relatively resistant to endogenous factor H and I-like activity (2-B), with distinct amounts of alpha' chain (C3b) persisting, but was still cleavable when extra factor H and I were added (2-D). The 43 kDa product indicates cleavage at Arg$^{1320}$, (a faint band at 71 kDa representing the other fragment of the alpha' chain could be seen in longer exposures) but no 68 kDa band was present, showing that this mutant is resistant to cleavage at the mutated Gln$^{1303}$.

4. The mutant C3M-26 (Arg$^{1303}$→Gln,Arg$^{1320}$→Gln) was cleavable by CVFBb an d the C3b-like product (alpha') was resistant to endogenous factor H and I-like activity (3-B). It was also very resistant to the additional factors H and I (3-D) in comparison with the unmutated C3 (1) and other mutants (2 and 4). There was a small amount of 46 kDa product indicating some cleavage at the mutated Gln$^{1303}$ (the accompanying 68 kDa fragment was also visible on longer exposures). There was little or no detectable 43 kDa that would correspond to any cleavage at Gln$^{1320}$. Therefore the Arg→Gln mutation at position 1303 is less effective than that at position 1320 at preventing cleavage by factor I. (This slow residual cleavage might also be occurring in the mutant C3M-I23 (Arg$^{1303}$→Gln), but the 46 kDa intermediate is probably being rapidly processed to 43 kDa by further cleavage at the unmutated Arg$^{1320}$.)

5. The mutant C3M-51 (Arg$^{1320}$→Gln) was cleavable by CVFBb and the product was cleaved by endogenous factor H and I-like activity (4-B), and by additional factor H and I (4-D). The 46 kDa product (and faint 68 kDa band) indicates cleavage at Arg$^{1303}$. However, the absence of a 43 kDa band indicates that it is not cleaved at the mutated Gln$^{1320}$.

EXAMPLE 5

Comparison of various amino acid substitutions at position 1303

1. Introduction

The previous examples described mutations of arg 1303 and arg 1320 to glutamine residues. Both mutations imparted resistance to cleavage at those positions by factor I. However, there was a small but detectable degree of cleavage at gln 1303. Therefore a number of other amino acid substitutions at this position have been made and tested. Cleavage occurs, in decreasing order of efficacy when residue 1303 is: Arg>Tyr>[Cys or Trp]>Gln>[Glu or Gly]. These results are unexpected because (i) all known naturally occurring human factor I-mediated cleavages occur C-terminal to arginine residues, so it would have been deduced that the enzyme had a requirement for arginine; and (ii) if it did cleave at other residues one would predict that they would have to be electrostatically similar to arg, i.e. a basic residue (lys or his), (e.g. trypsin selectively cleaves C-terminal to arg, lys or his), so one could not have predicted cleavage of the tyrosine substitution.

Therefore substitution of arg 1303 with glycine or glutamic acid is preferred for the purpose of creating a derivative of C3 resistant to inactivation by factor I.

2. Methods 2.1 Mutagenesis: the degenerate mutagenic primer used was:
caactgcccagc(gt)(ag)(cg)agctccaagatcacc (letters in brackets indicate mixture of bases at that position). Mutants were constructed either by the gapped-plasmid method (as described in the earlier examples), or by the "megaprimer method" (V. Picard et al, Nuc Acid Res 22:2587–91, (1994)), in which the upstream primer was caccaggaactgaatctagatgt-gtccctc and the downstream primer was gttttatggtgaccttaag-gtcgaatttatta. All mutations were performed on templates in which the C3-encoding DNA had already been mutated such that amino acid residue 1320 was glutamine, and a restriction site for AflII had been introduced at position 4149 (as described in the earlier examples) and were confirmed by DNA sequencing.

2.2 Expression: mutants were expressed in COS cells using the pcDNA3 vector as described in the earlier examples, biosynthetically labelled with [$^{35}$S] methionine in serum-free medium.

2.3 Assay: the supernatants were treated with CVFBb (formed by reaction of CVF with factors B and D in magnesium-containing buffer) and factors H and I followed by immunoprecipitation with anti-C3 and separation by SDS-polyacrylamide gel electrophoresis performed under reducing conditions (as described in the earlier examples). The gel was fixed, treated with Amersham "Amplify" reagent, dried and exposed to autoradiography film to yield the result shown in the figure.

3. Results

Factor I-mediated cleavage at position 1303 (site 1) without cleavage at 1320 (site 2) (where this has been mutated to glutamine) produces bands of 46 and 68 kDa. It can be seen that cleavage occurs in the order: arg(R)>tyr(Y)>cys(C) and trp(W)>gln(Q)>gly(G) and glu(E). The wild-type (arginine at both positions) is cleaved at both positions to produce fragments of 43 (too small to be visible on this gel) and 68 kDa.

4. Figure

The results are shown in FIG. 4. The residues at site 1 (position 1303) and site 2 (1320) are indicated above B the respective tracks.

EXAMPLE 6

Demonstration of enhanced resistance to inactivation by factors I and H after mutation of arg 1303 to gin 1. Introduction The earlier examples demonstrated that conversion of either arg 1303 or arg 1320 to glutamine made that site resistant to cleavage by factor I. Mutation of both sites makes a molecule that is resistant to cleavage at either site. Here, we further demonstrate that mutation of arg 1303 to gin alone (without alteration to arg 1320) results in a considerable resistance, compared to the wild-type, to functional inactivation by factors I and H.

2. Method 2.1 Expression: The preparation of the arg 1303→gln mutation was described in an earlier example. This was transfected into CHO (a common laboratory cell line derived from chinese hamster ovary cells) by the calcium phosphate method, and stable transfectants selected on the basis of resistance to G418 ("Geneticin" available from Sigma). Cell culture supernatants were collected, and the expressed C3 was partially purified by sodium sulphate precipitation (10–20% (w/v) fraction), and ion-exchange chromatography on Q-sepharose and mono-Q sepharose (A W Dodds Methods Enzymnol 223: 46 (1993)).

2.2 Assay: Sheep erythrocytes were coated with SO16 monoclonal antibody (R A Harrison and P J Lachmann Handbook of Experimental Immunology 4th Edition chpt. 39 (1986)) and 4.4 ml of a 5% (v/v) suspension was then incubated with approximately 10 μg C2, 24 μg C4 and 1 μg C1 (purified human components) for 10 min at 37° C. in CFD (R A Harrison and P J Lachman supra) . 0.8 ml of this mixture was then incubated for 105 min with 0.25 ml containing the semi-purified mutant or wild-type C3 and EDTA to a final concentration of 12.5 mM. The cells were then washed in CFD and used in CFD containing 0.1% (w/v) gelatin (CFD-gel). Radioligand binding with [$^{125}$I]-labelled clone 4 monoclonal anti-C3 antibody was used to confirm that similar amounts of wild-type or mutant C3b were deposited.

For the assay, 40 µl of a 5% suspension of cells was diluted in 250 µl CFD-gel and 50 µl aliquots were incubated with 50 µl CFD-gel containing dilutions of factors I and H to final concentrations of 100, 10, 1 and 0 µg/ml each, at 37° C. for 30 min. 0.9 ml of CFD was then added, the cells pelletted by centrifugation and washed twice more with 1 ml of CFD each time. The cells were then resuspended in 100 µl CFD-gel containing 100 µg/ml factor B, 100 µg/ml properdin, 1 µg/ml factor D and 0.3 mM NiCl$_2$. After 10 minutes at 37° C., 0.9 ml of CFD containing 10 mM EDTA and 2% (v/v) normal guinea-pig serum. After a further 30 min at 37° C., unlysed cells were pelletted by centrifugation, and the degree of lysis determined by measuring the absorbance of the supernatant at 412 nm. The absorbance equivalent to 100% lysis was determined from an aliquot of cells lysed in water, and hence the percentage lysis was calculated.

This assay measures the ability of deposited C3b to form a functional C3bBbP convertase. Conversion to iC3b prevents convertase formation and subsequent lysis in serum/EDTA.

3. Results

The result shown in the figure indicates that more than ten times as much factor I and factor H are required to abrogate the hemolytic activity of the arg 1303→gln mutant, when compared to the wild-type. This mutation is therefore advantageous for the creation of a derivative of C3 whose C3b product is resistant to inactivation by factors H and I. The effect could either be due to the greater resistance to cleavage at position 1303 (when arg is mutated to gln), or to greater resistance to cleavage at position 1320 when cleavage can first take place at position 1303.

4. Figure

The results are shown in FIG. 5. The x-axis indicates the concentration of factors H and I. Q1 represents the arg 1303→gln mutation. % lysis is measured as described in the methods.

Discussion

The essential features of Human C3, with respect to modified variants described herein are as follows:

(i) The molecule has a functionally C3b-like derivative in that it can combine with functionally active human factor B, which can then be cleaved by human factor D to form an enzyme capable of cleaving human C3.

(ii) The amino acid sequences of derivatives are more homologous to C3 from humans than to C3 from any other species for which a sequence is presently known, or to any other presently known protein sequence. Structural features of C3 present in wild-type protein, but not necessarily in modified derivatives, include the following:

(a) The DNA coding sequence and translated protein sequence for the variant of human C3 used in the examples of the invention described herein are given in FIGS. 2 and 1 respectively. This protein sequence differs from the published sequence [2] at just two amino acids (details are given in the examples). It is assumed that many more variations are compatible with C3 function, even though most will not be present in the population.

(b) The primary translation product is proteolytically processed into two disulphide-linked chains, alpha (residues 672–1663) and beta (residues 23–667), with removal of the signal sequence (residues 1–22).

(c) The mature protein contains a thiolester bond between residues Cys1010 and Gln1013.

(d) C3 convertases cleave C3 to remove C3a (residues 672–748). This reaction is followed by breakage of the thiolester bond.

(e) In the presence of factor H, factor I cleaves C3b between residues Arg1303 and Ser1304, and between Arg1320 and Ser1321.

Modifications Made to the Native C3 Molecule

Replacement of Arg1303 by Gln

This modification is at one site of cleavage of C3b by factor I. The effect is to reduce the rate of cleavage by factor I at this position. The change to glutamine was selected to take away the positive charge of the arginine, which is likely to be important for the serine protease activity of factor I, while retaining a hydrophilic character and a similar side-chain size that should minimise any disruptions to the tertiary protein structure. Evidence supporting this presumption is that the mutation did not prevent processing into a two-chain structure, formation of a thiolester or cleavage of C3 by C3 convertase. Mutation of Arg1303 to another amino acid can achieve a similar or even a superior effect, as demonstrated in Example 5.

It may also be possible to reduce this cleavage by mutating Ser1304 (the other side of the cleavage site) or other residues involved in the enzyme-substrate interaction.

Replacement of Arg1320 by Gln

This modification is at the other site of cleavage of C3b by factor I. The effect is to drastically reduce (virtually abolish) the rate of cleavage by factor I at this position. The change to glutamine was made on the same criteria described above, and this mutation also did not prevent processing into a two-chain structure, formation of a thiolester or cleavage of C3 by C3 convertase. Again, mutation to another amino acid may achieve the same effect, as may mutation of Ser1321 or other residues involved in the enzyme-substrate interaction.

When in combination the two mutations, Arg1303-Gln and Arg1320-Gln, protect the C3b from inactivation and hence maintain its ability to form part of an active C3bBb convertase. Other mutations (including combinations of mutations) that abolish both cleavage reactions could also be used (for example Arg 1303 Glu or Arg 1303 Gly could be used in combination with Arg 1320 Gln).

EXAMPLE 7

Various mutations that reduce the interaction of C3b/C3i with factor H 7.1 Introduction Other laboratories have produced evidence based either on the effects of synthetic peptides (Ganu, V. S. and Muller-Eberhard, H. J., 1985, Complement 2:27; Becherer, J. D. et al., 1992, Biochemistry 31: 1787–1794), or limited mutagenesis (Taniguchi-Sidle, A. and Isenman, D. E., 1994 J. Immunol. 153: 5285–5302) to suggest that the residues 752–761 in the primary sequence of the C3 transcript (see FIG. 1) could be involved in the interaction with factor H. However, other published evidence suggests that only residues 767–776 are involved in the interaction with factor H, whereas residues 752–761 are important for the interaction with factor B (Fishelson, 1991, Mol. Immunol. 28:545–552). We surmised that more extensive mutagenesis of this region might reduce the affinity for factor H and therefore be desirable for the objective of creating a C3 derivative that is resistant to factor H. Furthermore, we guessed that the important residues to mutate could be the prominent acidic residues (aspartic and glutamic acids) and that it would be desirable to change them to neutral residues less likely to mediate strong interactions. In this example we changed residue 752–754 from Asp-Glu-Asp to Gly-Ser-Gly, in combination with changing residues 758–760 from Glu-Glu-Asn to Gly-Ser-Gly. The product displayed reduced cleavage characteristics consistent with a reduction in the susceptibiliity to factor H. This provides evidence that C3 can be modified to reduce the binding of factor H, and hence the susceptibility to factors H and I. These modifications are desirable for the creation of a C3 convertase that is stable under physiological conditions.

7.2 Method

The methods of mutagenesis, expression and analysis have been described in the earlier examples. The mutagenic oligonucleotide that was synthesised had the sequence: agtaacctgggttcgggcatcattgcaggatcgggcatcgtttcc.

7.3 Results

The results of cleavage reactions are shown in FIG. 6. These indicate that:

1. Addition of CVFBb to wild-type C3 results in elimination of the alpha chain (track 2) because the C3b that is formed is susceptible to the low concentrations of factor I and H in the culture supernatant. C3i that has been formed during expression or this subsequent incubation has been broken down to iC3i in the same way. Addition of exogenous factors I and H (tracks 3 and 4) are therefore no different from tracks 1 and 2 respectively, because the medium itself contains sufficient factor H and I activity to effect complete cleavage.

2. In contrast, treatment of the mutant C3 with CVFBb (track 6) does not result in disappearance of the alpha chain. There is some generation of alpha', corresponding to C3b, but some or all of this remains, indicating that the persistence of alpha chain is not merely the result of a failure of cleavage by CVFBb. The remaining uncleaved alpha chain in track 2 may therefore represent C3i that has not been cleaved by the endogenous activities of factors H and I, although it is also possible that some of this represents native C3 persisting if the mutant has acquired a partial resistance to CVFBb. Addition of high concentrations of exogenous factors H and I (track 7 and 8) does produce depletion of alpha and alpha' chains, indicating that (i) the mutant is not completely resistant to these factors, and (ii) the alpha chain uncleaved by CVFBb in track 2 is predominantly derived from C3i (which is cleavable by factors H and I but not by CVFBb) rather than from native C3 (which is cleavable by CVFBb but not by factors H and I). Still not all the alpha chain is cleaved, even in track 8, probably because of the resistance to factors H and I.

Therefore mutation of residues 752–754, and residues 758–760 can generate a C3 molecule that can still be cleaved by C3 convertases, but is partially resistant to the actions of factors H and I. In view of other published data, this is most probably because the mutations have modified a region that is involved in the interaction with factor H and hence have resulted in a reduced affinity for factor H.

EXAMPLE 8

A site in C3 that can be mutated to modify the interaction of C3i with factor B 8.1 Introduction The previous examples have demonstrated that mutations to C3 can modulate the interactions with factors H and I. In order to discover other sites in C3 that might interact with factor B, we compared the known sequences of C3 molecules from different species, as well as with available sequences for C4 and other homologous proteins. We identified the region corresponding to residues 1427–1433 of human C3 that might be involved in C3 and C4 specific functions. This could include interaction with factor B (or its homologue, C2, in the case of C4), but not necessarily because other potential functions include thiolester formation, conversion into C3b (or C4b form), interaction with substrate C3 and/or C5 in convertase activity and interaction with factor I and its cofactors. Therefore selected residues were mutated to the corresponding residues (based on sequence alignments) found in another homologous protein, in this case human C5. Thus residue 1427 was changed from an Arg to a Gln, residue 1431 from a Lys to Asp, and residue 1433 from a Glu to a Gln. The resulting mutant was found to be susceptible to cleavage by C3 convertase (CVFBb) and the C3b product was cleavable by factors H and I. However, this mutant did not support the conversion of factor B to Bb plus Ba, which is dependent on the binding of factor B to C3i (or C3b). Therefore we have evidence that mutation of this region has diminished the interaction with factor B. Whilst this is undesirable for the generation of a super-active C3 convertase, it does provide an indication that other modifications to this region of C3 will also alter the interaction with factor B, and some of these will probably increase the affinity. As a consequence such mutations may also increase the stability and activity of the bimolecular convertase enzyme, C3bBb (or C3iBb).

8.2 Methods

The alignments shown in Table 1 overleaf illustrate why we considered that this region was a candidate for mutagenesis. We surmised that characters of certain residues were well conserved in C3 and C4 but distinctly different in the other proteins. Residues 1427, 1431 and 1433 were selected because their charged nature might be indicative of groups involved in protein-protein interactions. The changes were made to the corresponding residues in human C5 because these displayed very different electrostatic properties, but within the context of some other conserved residues that might indicate a similar local structure.

TABLE 1

Alignments of sequences of C3 and related molecules for region of residues 1427–1435 of human C3

| Protein | Species | RESIDUE (Human) | | | | | | | | |
|---|---|---|---|---|---|---|---|---|---|---|
| | | 1427 | 1428 | 1429 | 1430 | 1431 | 1432 | 1433 | 1434 | 1435 |
| C3 | Human | R | Y | I | S | K | Y | E | L | D |
| | Mouse | R | Y | I | S | K | Y | E | M | N |
| | Rat | R | Y | I | S | K | Y | E | M | D |

TABLE 1-continued

Alignments of sequences of C3 and related molecules
for region of residues 1427–1435 of human C3

| Protein | Species | RESIDUE (Human) | | | | | | | | |
|---|---|---|---|---|---|---|---|---|---|---|
| | | 1427 | 1428 | 1429 | 1430 | 1431 | 1432 | 1433 | 1434 | 1435 |
| | G. pig | R | Y | I | S | K | Y | E | L | D |
| | Rabbit | R | Y | I | S | K | Y | E | L | N |
| | Cobra | R | Y | I | S | K | F | E | I | D |
| | Xenopus | K | Y | I | S | K | Y | E | V | N |
| | Trout | R | Y | I | E | K | F | E | M | D |
| C4 | Human | R | Y | V | S | H | F | E | T | E |
| | Mouse | R | Y | V | S | H | F | E | T | D |
| Slp | Mouse | R | Y | V | S | H | F | E | T | D |
| C3/C4-like | Haglish | N | Y | I | V | Q | Y | E | I | R |
| | Lamprey | K | Y | I | S | N | Y | E | I | T |
| C5 | Human | Q | L | F | T | D | Y | Q | I | K |
| | Mouse | Q | L | L | T | D | Y | Q | I | K |
| A2M | Human | P | T | V | K | M | L | E | R | S |
| | Mouse | P | S | V | K | R | L | Q | D | Q |
| | Rat | P | T | V | K | M | L | E | R | S |
| PZP | Human | P | T | V | K | M | L | E | R | S |
| Murinoglobulin | Mouse | P | T | V | K | K | L | E | R | L |
| A1M | Rat | P | S | V | K | K | L | Q | D | Q |
| A1M | G. Hamster | P | T | V | K | K | L | E | R | S |
| A1I3 | Rat | P | T | V | K | K | L | E | R | L |

The methods of mutagenesis, expression and analysis of C3 cleavage reactions were as described in the earlier examples (Examples 1–4). The mutagenic oligonucleotide was synthesised with the sequence: tggtgttgaccaatacatctc-cgactatcagctggacaa.

Assay for Turnover of Factor B.

The expressed product was purified from the COS cell medium by affinity purification on a column of Clone-3-Sepharose as described in Example 9. This method results in considerable conversion of the thiolester broken form, C3i. Wild-type C3 was isolated by the same procedure. Dilutions of the wild-type C3 (⅕, ¹/25 and ¹/125) were run on an SDS-PAGE gel (reducing conditions) along with the mutant C3, and silver staining indicated that the mutant was present at a concentration equivalent to slightly less than the ¹/25 but much more than the ¹/125 dilution of wild-type. The same dilutions were used in the assay of factor B turnover. 5 µl of these C3's were incubated with 25 µl of CFD-G containing 5 µg/ml factor D and approximately 1.6 µg/ml of $^{125}$-labelled factor B (approx. 1000–2000 dpm/µl) for 3 h at 37° C. The samples were then analysed by SDS-PAGE (reducing conditions) with autoradiography of the dried gel. The results are shown in FIG. 7.

8.3 Results

As shown in FIG. 7, distinct cleavage of factor B occurs even at a ¹/125 dilution of the wild-type C3 (C3i). In contrast, no significant cleavage was observed in the presence of the mutant C3, even undiluted which should be at a concentration higher than the ¹/125 sample of the wild-type.

This mutant therefore appears to have an impaired ability to support the cleavage of factor B, most likely due to a reduction in its binding affinity for factor B. Therefore this is a region of C3 that can be mutated to modulate the interaction between C3i (or C3b) and factor B and perhaps also the stability of the convertase (C3iBb or C3bBb).

EXAMPLE 9

Purification of expressed mutant C3 molecules 9.1 Introduction

This example demonstrates how the mutant C3 molecules may be isolated from an expression medium, such as the culture medium of transfected eukaryotic cells. By simple affinity purification the C3 molecules are obtained in sufficient purity for functional tests and for conjugation to antibody by the method described in Example 10. Although elution from an antibody is accompanied by hydrolysis of a considerable proportion of the internal thiolester, the C3i product is still a suitable precursor for the generation of an active C3 convertase, as well as for the production of C3i-antibody conjugates. This approach is also likely to be useful as part of the preparation required for in vivo use.

9.2 Method

Affinity-purification on Clone-3-Sepharose.

Clone-3 is a rat monoclonal antibody that is specific for C3 and its derivatives, including C3b and C3i (Lachmann, P. J. et al., 1980, J. Immunol. 41:503–515). Other monoclonal antibodies against C3 are available, and in some cases have been successfully used to isolate C3 from small quantities of human plasma (Dodds, A. W., 1993, Methods Enzymol. 223:46–61) and are therefore also likely to be applicable for the isolation of molecules expressed ex vivo. The IgG fraction was coupled to Sepharose CL-4B using cyanogen bromide (methodology may be found in Harrison and Lachmann, 1986, Handbook of Experomental Immunology, 4th edn., Ed.s Weir, Herzenberg, Blackwell and Herzenberg; Blackwell, oxford). Culture supernatants were either passed directly through a column of this resin (re-circulated), or first con centrated by precipitation with 25% (w/v) $Na_2SO_4$, and resolubilization and dialysis into PBS, 5 mM $NaN_3$. The column is then washed successively with (i) PBS, 5 mM $NaN_3$ and (ii) PBS containing 1 M NaCl. Bound C3 elutes with 50 mnM Na borate buffer, pH 10.5, and is immediately neutralised by collection of 0.9 ml fractions into 0.1 ml 1 M Tris/HCl pH 7. The material is then dialysed into PBS, 5 mM $NaN_3$.

Preparation of C3 Bearing a "His-Tag"

A "His-Tag" is a string of histidine residues that displays affinity for columns bearing Nickel ions. This method has been employed to aid the isolation of expressed proteins. We thought that this could be useful for the isolation of expressed mutant C3 molecules so we have used insertion mutagenesis to generate a plasmid encoding C3 with a tail of 6 histidine residues at the carboxy terminus (immediately carboxy-terminal to residue 1663). This location for the his tag was selected so as to minimise interference with the synthesis, folding, processing and disulphide bond formation of the nascent C3. Residue 1661 is a cysteine residue that is involved in a disulphide bond to a residue earlier in the sequence (probably Cys 1537; Dolmer, K. and Sottrup-Jensen, L., 1993, FEBS-Lett 315: 85–90) and therefore it seemed prudent to make the insertion beyond this structural feature. The mutation was introduced using the "gapped-plasmid" technique used in Example 1, using the mutagenic oligonucleotide synthesised with the sequence: tgggtgc-cccaaccatcatcatcatcatcattgaccacaccccc.

Incorporation of the correct sequence was confirmed by DNA sequencing. This DNA sequence may now be transferred to an expression vector. After transfection of eukaryotic cells, it should be possible to isolate the expressed C3 by affinity for a column bearing Nickel ions, or by any other matrix with specific affinity for the "His-Tag".

9.3 Results

A number of mutant C3 have been purified on the Clone-3-Sepharose, including those described in Examples 1 and 2 expressed in CHO cells. The products retained the ability to support the cleavage of factor B by factor D. The same method was used to isolate the mutant described in Example B2, expressed in COS cells. Silver-staining of SDS-PAGE gels indicated that the isolated products were not 100% pure, but often appeared to be greater than or equal to 50% pure. This comes from starting materials generally containing less than 10 $\mu$g/ml C3 in 10% (v/v) fetal calf serum plus other cellular proteins. In addition the C3's were not degraded during isolation, and endogenous factor H and I activity appeared to have been removed.

Purification by virtue of the "His-Tag" involves milder elution conditions from a column bearing Nickel ions. For example, EDTA has been used. Application of this method to C3 should therefore allow isolation without rupture of the internal thiolester bond.

EXAMPLE 10

Conjugation of C3i to antibody and use to target C3 convertase activity against a particular cell 10.1 Introduction One aspect of the invention is that stable C3 convertases derived from mutant C3 molecules will cause enhanced C3 conversion which, if localised at a particular target site, will promote complement-dependent attack of that target. The favoured approach for targeting the response is to couple the mutant C3 molecule, as either the C3i or C3b derivative, to an antibody specific for the desired target. In this example we demonstrate a working methodology for formation of such conjugates, which is applicable to mutant C3i or C3b molecules and can be used on material affinity-purified from an expression system, even if the thiolester of C3 has been broken in the process. By coupling C3i to an antibody that specifically binds to sheep erythrocytes, we further show that the the conjugate fixes C3i to the erythrocyte surface such that a convertase, C3iBbP, can be formed that initiates lysis of these cells when other complement components are supplied in the form of normal guinea-pig serum (in EDTA to prevent de-novo formation of C3 convertases). Hence conjugation to antibody can be used to target a C3i molecule to initiate complement-dependent attack of a particular cell type. This example uses wild-type C3i, from human plasma, that forma a C3 convertase in vitro. In vivo, wild-type C3i and C3b are broken down by factor H and I. Therefore a mutant C3, constructed according to the plans in this patent to be resistant to factors H and I and therefore forming a stable C3 convertase, would be advantageous in a physiological context.

10.2 Method (i) Generation and purification of C3i-antibody conjugate

The antibody used was the IgG fraction isolated from a polyclonal rabbit anti-sheep erythrocyte antiserum. 1.1 mg was incubated with 75 nmol of SPDP in conjugation buffer, pH 7.5 (20 mM $KH_2PO_4$, 60 mM $Na_2HPO_4$, 0.12 M NaCl) for 2 h at room temperature. The PDP-IgG was purified by gel-filtration on a Superose-6 column (Pharmacia) (in a phosphate buffer, pH 7.4, containing 0.5 M NaCl). Reduction of a sample with dithiothreitol was used to estimate 4 PDP groups coupled per molecule of IgG. C3i was prepared by treatment of purified C3 with 0.1 M methylamine, pH 7.2 (2 h at 37° C.). Excess methylamine was removed by gel-filtration followed by dialysis into conjugation buffer. 18 nmole of C3i was mixed with 1.7 nmoles of PDP-IgG in 1.26 ml conjugation buffer and incubated for 1 day at room temperature followed by 1.5 days at 4° C. FIG. 8 shows a Coomassie Blue stained SDS-PAGE gel of the conjugation reaction mixture showing the appearance of a species of approximately 350 kDa that was not present in either PDP-IgG or C3i. This species was partially purified by gel-filtration on the Superose-6 column in a phosphate buffer, pH 7.4, containing 0.5 M NaCl and then dialysed into PBS. It eluted before the C3, in a volume from which a molecular weight of 300–400 kDa could be estimated by calibration with globular molecular weight standards. Concentrations of conjugate, free antibody and uncoupled C3 were estimated from a Coomassie-stained SDS-PAGE gel (non-reducing conditions). Two-dimensional SDS-PAGE (first dimension unreduced, second dimension reduced) revealed a pattern compatible with a 1:1 conjugate between IgG and C3i.

(ii) Demonstration that the C3-antibody conjugate can be used to target convertase activity against a particular cell.

20 $\mu$l of dilutions of the conjugate (0 (no conjugate), 1/100, 1/50, 1/10) were incubated with 100 $\mu$l of approximately 1% (v/v) sheep erythrocytes (prewashed in CFD) for 1 hour at 37° C. Parallel incubations were performed with equivalent amounts of PDP-IgG (no C3) and C3 alone. The cells were then washed 4 times in CFD and resuspended to 100 $\mu$l in CFD-G. 50 $\mu$l of this were lysed with 150 $\mu$l $H_2O$, followed by addition of 800 $\mu$l of CFD containing 10 mM EDTA and 2% (v/v) NGPS. The other 50 $\mu$l of conjugate-coated cells were incubated for 15 min at 370° C. with 50 $\mu$l of CFD-G containing 190 $\mu$g/ml factor B, 2 $\mu$g/ml factor D, 20 $\mu$g/ml properdin and 0.6 mM $NiCl_2$, followed by lysis with 900 $\mu$l of CFD containing 10 mM EDTA and 2% (v/v) NGPS. After 30 min at 37° C., the cells were pelleted by centrifugation (2000×g, about 3 min) and the optical absorbance of the supernatant was measured at 412 nm. Using the $H_2O$-treated samples as 100% lysis, and a buffer blank devoid of cells, the % lysis was calculated, as shown in FIG. 9. The conjugate produced dose-dependent lysis, whereas neither the PDP-IgG nor the C3i alone generated any lysis significantly above that observed in the absence of any such treatment.

10.3 Summary of Results

The method used has proved successful for coupling C3i to IgG as shown by:

1. The formation of a band of appropriate size (about 350 kDa) for a 1:1 C3:IgG conjugate shown by SDS-PAGE in FIG. 8.
2. Two-dimensional SDS-PAGE (first dimension non-reduced, second dimension reduced) indicated that this species contained both IgG and C3i.

3. The elution characteristic of this species on gel-filtration is again consistent with a molecule of about 350 kDa.
4. The conjugate displays a haemolytic activity that is not displayed by either PDP-IgG or C3i (FIG. 9).

The haemolytic assay (FIG. 9) further demonstrates that:
1. The specific anti-sheep erythrocyte antibody has localised the C3i to the target cell (sheep erythrocyte) membrane, preventing it from being removed by washing (in contrast to free C3i).
2. The conjugate retains the activity of the C3i in that it is still able to form a C3 convertase by reaction with properdin and factors B and D.
3. This convertase can initiate complement-dependent attack of the target, in this case by activating the lytic pathway (C5–9) to lyse the erythrocyte.

Additional data from other laboratories show that cobra venom factor can be coupled to an antibody and that these conjugates can target complement activation against a particular cell type (Vogel, 1988, Targeted. Diagn. Ther., 1:191–224; Muller, B. and Muller-Ruchholtz, W., 1987, Leuk. Res. 11:461–468; Parker, C. J., White, V. F. and Falk, R. J., 1986, Complement 3:223–235; Petrella, E. C. et al, 1987, J. Immunol. Methods 104:159–172). These data support the contention that C3 modified so that it is capable of forming a stable C3 convertase, like cobra venom factor, could be used to target complement-mediated responses, as outlined in this invention.

EXAMPLE 11

Demonstration that mutant C3 molecules induce factor B turnover in normal human serum 11.1 Introduction A major purpose of the invention described herein is the consumptive depletion of complement activity from biological fluids. The invention describes methods for the manufacture of C3 molecules that are resistant to down-regulation by factors H and I. In this state they will bind factor B and generate active C3 convertases. The activity of these convertases is demonstrated by the haemolytic assay employed in Example 6. Such a convertase will therefore consume C3. If the convertase is unstable, it will dissociate without much C3 conversion. However this will allow binding of fresh factor B, and its conversion to Bb and Ba. Thus the mutant C3 will promote the consumption of factor B, leading ultimately to the disablement of the alternative pathway, and its inability to amplify classical pathway stimulation. If a stable C3 convertase is formed, turnover of factor B will be reduced, but consumption of C3 will be increased. Both situations can therefore be desirable. In this example we demonstrate that mutant C3 molecules that are modified to make them resistant to factor I, but without any modification to modify the stability of the convertase, promote accelerated turnover of factor B in human serum. Wild-type C3, in contrast, causes no significant turn-over, presumably because wild-type C3i is rapidly degraded by factors H and I.

11.2 Method

The Mutants prepared are as follows:

Q1R2 Arg1303 changed to Gln (Example 2)

Q1Q2 Arg1303 changed to Gln, plus Arg1320 changed to Gln (Example 1)

E1Q2 Arg1303 changed to Glu, plus Arg1320 changed to Gln (Example 5)

These mutants were all expressed in CHO cells and then purified by precipitation with $Na_2SO_4$, followed by affinity purification on Clone-3-Sepharose, as described in Example B3. Wild-type C3 (R1R2) was similarly isolated. By SDS-PAGE with silver-staining, the concentration of Q1 was between 1/5 and 1/25 of the wild-type, the concentration of Q1Q2 was about that of 1/5 wild-type, and the concentration of E1Q2 was between 1/25 and 1/125 of wild-type. All preparations probably contained a majority of thiolester-broken molecules (C3i). 10 $\mu$of these C3 preparations were incubated with 10 $\mu$l of a solution of 20% (v/v) normal human serum in PBS containing 1 mM $MgCl_2$ and approximately 300 ng $^{125}$I-labelled factor B (approx. 2–300,000 dpm) for 1 hour at 37° C. 5 $\mu$l was then analysed by SDS-PAGE (reducing conditions). The dried gel was exposed to autoradiography film to indicate the positions of the bands corresponding to the intact factor B and its cleavage products. These were then excised and counted to accurately determine the degree of cleavage. The value obtained in buffer alone was subtracted as background (encompassing not only background cleavage, but also degradation products and other impurities present in the radioligand preparation.

11.3 Results

The resulting degrees of factor B cleavage are shown below:

| | |
|---|---|
| 1/25 Wild-type | 1.49% |
| 1/5 Wild-type | 2.74% |
| Q1R2 | 6.19% |
| Q1Q2 | 7.41% |
| E1Q2 | 6.42% |

Therefore the factor I resistant mutants all produce greater levels of factor B cleavage than equivalent amounts of wild-type C3 (C3i). With larger doses or longer incubations, complete incapacitation of the alternative pathway should result.

The abbreviations used in the foregoing examples include:

CFD, complement fixation diluent (defined in Harrison and Lachmann, 1986, Handbook of Experimental Immunology, 4th edn., Ed.s Weir, Herzenberg, Blackwell and Herzenberg; Blackwell, Oxford); CFD-G, CFD containing 0.1% (w/v) gelatin; PBS, phosphate-buffered saline; NGPS, normal guinea-pig serum; SDS-PAGE, SDS-polyacrylamide gel electrophoresis; SPDP, N-Succinimidyl-3-[2-pyridyldithio]propionate.

REFERENCES:

1. Bergmann, M. & Fruton, J. S. (1941) Adv. Enzymol., 1:63–98.
2. de Bruijn, M. H. & Fey, G. H. (1985), Proc. Natl. Acad. Sci. U.S.A. 82:708–712
3. Crawford-M H et al. (1988) Circulation. 78:1449–58
4. Daha, M. R. & van Es, L. A. (1982) Immunol. 43:33–38.
5. Farries, T C; Lachmann, P J & Harrison, R A (1988) Biochem. J. 252:47–54
6. Farries, T C; Lachmann, P J & Harrison, R A (1988) Biochem. J. 253:667–75
7. Forty, J; Hasan, R; Cary, N; White, D J & Wallwork, J (1992) Transplant. Proc. 24:488–9
8. Fritzinger, D. C. et al. (1992) J. Immunol. 149:3554–3562
9. Harrison, R. A. & Lachmann, P. J. (1980) Mol. Immunol. 17:9–20.

10. Kalli, K. R., Hsu, P. & Fearon, D. T. (1994) Springer Semin. Immunopathol. 15:417–431.
11. Kinoshita, T; Takata, Y; Kozono, H; Takeda, J; Hong, K S & Inoue, K (1988) J. Immunol. 141:3895–901
12. McNearney, T A; Odell, C; Holers, V M; Spear, P G; Atkinson, J P (1987) J. Exp. Med. 166:1525–35
13. Nicol, P. A. E. & Lachmann, P. J. (1973) Immunol. 24:259–275
14. Pangburn, M K & Muller-Eberhard, H J (1984) Springer Semin. Immunopathol. 7:163–92
15. Rother, K. & Till, G. O. (eds) (1988) "The complement System" (Springer-Verlag Berlin Heidelberg, Germany)
16. Van den Berg, C. W., Aerts, P. C. & Van Dijk, H. (1991) J. Immunol. Methods 136:287–294.
17. Vogel, C W; Smith, C A & Muller-Eberhard, H J (1984) J. Immunol. 133:3235–41
18. Weisman, H F et al. (1990) Science 249:146–51.
19. Wu, R. (ed.) (1993) Methods Enzymol. 217: ch.s 12–14 (Academic Press, San Diego, U.S.A.)
20. Botto, M, Fong, K. Y., So, A. K., Koch, C. & Walport, M. J. (1990) J. Exp. Med. 172:1011–7
21. Sambrook, J., Fritsch, E. F. & Maniatis, T. (1989) "Molecular Cloning. A Laboratory Manual" second edition (Cold Spring Harbor Laboratory Press)
22. Fishelson, Z. (1991) Mol. Immunol. 28:545–52.
23. Taniguchi-Sidle, A & Isenman, D. E. (1993) Mol. Immunol. 30:54.
24. Lambris, J. D., Avila, D., Becherer, J. D. & Muller, Eberhard, H. J. (1988) J. Biol. Chem. 263:12147–50.
25. Taniguchi-Sidle, A. and Isenman, D. E. (1992) J. Biol. Chem. 267:635–643.
26. Hofer, B. and Kuhlein, B. (1993) Methods Enzymol. 217:173–189.
27. Morinaga, Y., Franceschini, T., Inouye, S. and Inouye, M. (1984) Bio-technology 2:636–639.
28. Harrison, R. A. and Lachmann, P. J. (1986) "Handbook of Experimental Immunology" (eds Weir, Herzenberg, Blackwell and Herzenberg; Blackwell, Oxford) 4th ed.,
29. Kotwal, G., J., and Moss, B., Nature (1988) 335 (6186):176–8.

What is claimed is:

1. A DNA sequence encoding a modified human C3 protein which is capable of forming a stable C3 convertase wherein said modified protein is selected from the group consisting of:

(a) a C3 protein in which either Arg-1303, Arg-1320, or both is replaced with another amino acid;
(b) a C3 protein which has reduced susceptibility to Factor H and/or Factor I relative to native human C3 convertase, said protein having one or more amino acid changes relative to native human C3 convertase in the region corresponding to amino acid residues 752–754 and/or residues 758–780 of native human C3 convertase; and (c) a C3 protein having amino acid changes relative to native human C3 convertase at amino acid residues 1427, 1431 and/or 1433 of native human C3 convertase.

2. A DNA sequence coding for a protein as claimed in claim 1, wherein the protein is modified by replacement of either Arg-1303, Arg-1320, or both by another amino acid.

3. A DNA sequence coding for a protein as claimed in claim 2, wherein Arg-1303, Arg-1320 or both are replaced by glutamine, tyrosine, cystene, tryptophan, glutamic acid or glycine.

4. A DNA sequence coding for a protein as claimed in claims 2 or 3, wherein Arg-1320 is replaced by glutamine.

5. A DNA sequence coding for a protein as claimed in claim 2, wherein Arg-1303 is replaced by glutamic acid, glycine or glutamine.

6. A DNA sequence coding for a protein as claimed in claim 1, wherein the protein has reduced susceptibility to Factor H and/or Factor I relative to native human C3 convertase, said protein having one or more amino acid changes relative to native human C3 convertase in the region corresponding to amino residues 752–754 and/or residues 758–780 of native human C3 convertase.

7. A DNA sequence coding for a protein as claimed in claim 6, wherein the one or more amino acid changes are changes from acidic amino acid residues to neutral amino acid residues.

8. A DNA sequence coding for a protein as claimed in claim 7, wherein the amino acid residue changes are changes from Asp-Glu-Asp to Gly-Ser-Gly.

9. A DNA sequence coding for a protein as claimed in claim 1, wherein the protein has amino acid changes relative to native human C3 convertase at amino acid residues 1427, 1431 and/or 1433 of native human C3 convertase.

10. A vector comprising the DNA sequence of claim 1.

* * * * *